(12) United States Patent
Anderson et al.

(10) Patent No.: US 9,770,399 B2
(45) Date of Patent: *Sep. 26, 2017

(54) HAIR CARE COMPOSITIONS AND METHODS OF TREATING HAIR

(71) Applicant: Living Proof, Inc., Cambridge, MA (US)

(72) Inventors: Daniel Griffith Anderson, Sudbury, MA (US); Amir Nashat, Newton, MA (US); Mitchell John DeRosa, Hyde Park, MA (US); David Thomas Puerta, Carlsbad, CA (US); Ronald P. McLaughlin, Reading, MA (US); Bryan Scott Akcasu, Burbank, CA (US); Susan Alice Thiell, Natick, MA (US); Richard Matthew Ramirez, Wichita Falls, TX (US)

(73) Assignee: Living Proof, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/974,411

(22) Filed: Aug. 23, 2013

(65) Prior Publication Data

US 2013/0336913 A1 Dec. 19, 2013

Related U.S. Application Data

(60) Division of application No. 12/797,141, filed on Jun. 9, 2010, now Pat. No. 8,551,463, which is a continuation of application No. PCT/US2008/080819, filed on Oct. 22, 2008, which is a continuation-in-part of application No. 12/147,397, filed on Jun. 26, 2008, now Pat. No. 8,226,934.

(60) Provisional application No. 60/981,625, filed on Oct. 22, 2007, provisional application No. 60/981,632, filed on Oct. 22, 2007.

(51) Int. Cl.
| | |
|---|---|
| *A61Q 5/00* | (2006.01) |
| *A61Q 5/12* | (2006.01) |
| *A61K 8/70* | (2006.01) |
| *A61K 8/37* | (2006.01) |
| *A61K 8/69* | (2006.01) |
| *A61K 8/81* | (2006.01) |

(52) U.S. Cl.
CPC ............... *A61K 8/70* (2013.01); *A61K 8/37* (2013.01); *A61K 8/69* (2013.01); *A61K 8/8152* (2013.01); *A61Q 5/00* (2013.01); *A61Q 5/12* (2013.01)

(58) Field of Classification Search
None
See application file for complete search history.

(56) References Cited

U.S. PATENT DOCUMENTS

| | | |
|---|---|---|
| 2,396,278 A | 3/1946 | Lind |
| 2,438,091 A | 3/1948 | Lynch |
| 2,486,921 A | 11/1949 | Byerly |
| 2,486,922 A | 11/1949 | Strain |
| 2,528,378 A | 10/1950 | Mannheimer |
| 2,658,072 A | 11/1953 | Kosmin |
| 3,155,591 A | 11/1964 | Hilfer |
| 3,332,880 A | 7/1967 | Kessler et al. |
| 3,405,084 A | 10/1968 | Bohac et al. |
| 3,577,517 A | 5/1971 | Kubot et al. |
| 3,633,591 A | 1/1972 | Anzuino et al. |
| 3,634,022 A | 1/1972 | Robbins et al. |
| 3,634,367 A | 1/1972 | Lang et al. |
| 3,676,550 A | 7/1972 | Anzuino |
| 3,726,288 A | 4/1973 | Nowak et al. |
| 3,810,977 A | 5/1974 | Levine et al. |
| 3,862,306 A | 1/1975 | Block et al. |
| 3,927,199 A | 12/1975 | Micchelli et al. |
| 3,929,678 A | 12/1975 | Laughlin et al. |
| 3,959,461 A | 5/1976 | Bailey et al. |
| 3,981,987 A | 9/1976 | Linke et al. |
| 3,993,744 A | 11/1976 | Cella et al. |
| 3,993,745 A | 11/1976 | Cella et al. |
| 4,013,786 A | 3/1977 | Cella et al. |
| 4,044,121 A | 8/1977 | Ko |
| 4,059,688 A | 11/1977 | Rosenberg et al. |
| 4,077,441 A | 3/1978 | Rosen et al. |
| 4,098,811 A | 7/1978 | Falk |
| 4,122,029 A | 10/1978 | Gee et al. |
| 4,164,562 A | 8/1979 | Nandagiri et al. |
| 4,176,176 A | 11/1979 | Cella et al. |
| 4,192,861 A | 3/1980 | Micchelli et al. |
| 4,196,190 A | 4/1980 | Gehman et al. |
| 4,237,253 A | 12/1980 | Jacquet et al. |
| 4,243,548 A | 1/1981 | Heeb et al. |
| 4,265,878 A | 5/1981 | Keil |
| 4,275,055 A | 6/1981 | Nachtigal et al. |
| 4,315,910 A | 2/1982 | Nowak, Jr. et al. |
| 4,348,380 A | 9/1982 | Jacquet et al. |
| 4,358,567 A | 11/1982 | Hayama et al. |
| 4,387,090 A | 6/1983 | Bolich, Jr. |
| 4,399,077 A | 8/1983 | Vanlerberghe et al. |
| 4,421,769 A | 12/1983 | Dixon et al. |
| 4,521,404 A | 6/1985 | Lorenz et al. |
| 4,543,249 A | 9/1985 | Nelson |
| 4,567,035 A | 1/1986 | Waxman et al. |
| 4,584,196 A | 4/1986 | Vanlerberghe et al. |

(Continued)

FOREIGN PATENT DOCUMENTS

| | | |
|---|---|---|
| DE | 19856567 A1 | 6/2000 |
| EP | 408442 B1 | 8/1994 |

(Continued)

OTHER PUBLICATIONS

Office Action in Canadian Patent Application No. 2,703,168, dated Dec. 12, 2011.

(Continued)

Primary Examiner — Jyothsna Venkat
(74) Attorney, Agent, or Firm — Troutman Sanders LLP

(57) ABSTRACT

The present invention provides compositions, kits and methods for treating scalp hair. The compositions include fluorinated (but not perfluorinated), non-polymeric compounds in a suitable excipient to provide beneficial effects on hair.

23 Claims, 3 Drawing Sheets

(56) References Cited

U.S. PATENT DOCUMENTS

| | | |
|---|---|---|
| 4,689,379 A | 8/1987 | Chuang |
| 4,767,613 A | 8/1988 | Nuber et al. |
| 4,778,675 A | 10/1988 | Vanlerberghe et al. |
| 4,803,067 A | 2/1989 | Brunetta et al. |
| 4,850,577 A | 7/1989 | Yamaoka |
| 4,874,604 A | 10/1989 | Sramek |
| 4,880,620 A | 11/1989 | Vanlerberghe et al. |
| 4,897,262 A | 1/1990 | Nandagiri et al. |
| 4,923,695 A | 5/1990 | Nowak, Jr. et al. |
| 4,954,336 A | 9/1990 | Chuang et al. |
| 5,021,238 A | 6/1991 | Martino et al. |
| 5,082,010 A | 1/1992 | Skaryd et al. |
| 5,183,588 A | 2/1993 | Salerno et al. |
| 5,183,589 A | 2/1993 | Brunetta et al. |
| 5,206,298 A | 4/1993 | Kawaguchi |
| 5,288,825 A | 2/1994 | Toyooka et al. |
| 5,312,968 A | 5/1994 | O'Lenick, Jr. et al. |
| 5,523,078 A | 6/1996 | Baylin |
| 5,688,493 A | 11/1997 | Sugawara et al. |
| 5,705,148 A | 1/1998 | Bollens et al. |
| 5,714,642 A | 2/1998 | Didion et al. |
| 5,738,879 A | 4/1998 | Rine |
| 5,741,499 A | 4/1998 | Arnauld et al. |
| 5,833,997 A | 11/1998 | Mahieu et al. |
| 5,851,544 A | 12/1998 | Penska et al. |
| 5,939,370 A | 8/1999 | Petit et al. |
| 5,989,533 A | 11/1999 | Deegan et al. |
| 6,002,048 A | 12/1999 | Fujii et al. |
| 6,060,626 A | 5/2000 | Fujii et al. |
| 6,132,736 A | 10/2000 | Mellul et al. |
| 6,156,296 A | 12/2000 | Riedel et al. |
| 6,362,378 B1 | 3/2002 | Jacquot et al. |
| 6,410,005 B1 | 6/2002 | Galleguillos et al. |
| 6,419,937 B1 | 7/2002 | Waldmann-Laue et al. |
| 6,455,058 B1 | 9/2002 | Sun et al. |
| 6,602,495 B2 | 8/2003 | Bergmann et al. |
| 6,653,353 B2 | 11/2003 | Adams et al. |
| 6,706,674 B2 | 3/2004 | Cincotta et al. |
| 6,846,812 B2 | 1/2005 | Dalko et al. |
| 6,884,265 B2 | 4/2005 | Vidal et al. |
| 6,939,922 B2 | 9/2005 | Beckley et al. |
| 7,045,608 B2 | 5/2006 | Eliu et al. |
| 7,135,168 B2 | 11/2006 | Miczewski et al. |
| 7,204,861 B2 | 4/2007 | Marsh et al. |
| 7,288,121 B2 | 10/2007 | Greaves et al. |
| 7,300,471 B2 | 11/2007 | Greaves et al. |
| 7,303,591 B2 | 12/2007 | Greaves et al. |
| 7,377,946 B2 | 5/2008 | Gourlaouen et al. |
| 7,429,575 B2 | 9/2008 | Yu et al. |
| 7,572,776 B2 | 8/2009 | Yu et al. |
| 7,635,394 B2 | 12/2009 | Fadli et al. |
| 7,763,240 B2 | 7/2010 | Anderson et al. |
| 7,776,844 B2 | 8/2010 | Yu et al. |
| 7,785,575 B2 | 8/2010 | Anderson et al. |
| 7,857,864 B2 | 12/2010 | Fadli et al. |
| 7,985,744 B2 | 7/2011 | Morikawa et al. |
| 8,226,934 B2 * | 7/2012 | Anderson ............ A61K 8/8152 424/47 |
| 8,242,309 B2 | 8/2012 | Puerta et al. |
| 8,318,138 B2 * | 11/2012 | Anderson et al. ............... 424/47 |
| 8,404,221 B2 | 3/2013 | Puerta et al. |
| 8,404,676 B2 | 3/2013 | Montagne et al. |
| 8,545,818 B2 * | 10/2013 | Anderson ............ A61K 8/8152 424/47 |
| 8,551,463 B2 | 10/2013 | Anderson et al. |
| 8,557,223 B2 | 10/2013 | Anderson et al. |
| 8,889,668 B2 | 11/2014 | Montagne et al. |
| 9,138,398 B2 | 9/2015 | Puerta et al. |
| 9,192,553 B2 * | 11/2015 | Anderson ............ A61K 8/8152 |
| 9,326,926 B2 | 5/2016 | Pressly et al. |
| 9,351,964 B2 | 5/2016 | Almstead et al. |
| 2002/0086167 A1 | 7/2002 | Hayashi et al. |
| 2002/0197227 A1 | 12/2002 | Scholz |
| 2003/0147830 A1 | 8/2003 | Phillips et al. |
| 2003/0175229 A1 | 9/2003 | Giroud |
| 2004/0040095 A1 | 3/2004 | King et al. |
| 2005/0251923 A1 | 11/2005 | Greaves et al. |
| 2006/0057075 A1 * | 3/2006 | Arkin ..................... A61K 8/046 424/47 |
| 2006/0078522 A1 | 4/2006 | Vic |
| 2006/0078523 A1 | 4/2006 | Vic et al. |
| 2006/0080792 A1 | 4/2006 | Vic et al. |
| 2006/0083706 A1 | 4/2006 | Vic et al. |
| 2006/0083762 A1 | 4/2006 | Brun et al. |
| 2006/0085922 A1 | 4/2006 | Plos |
| 2006/0088488 A1 | 4/2006 | Brun |
| 2006/0088493 A1 | 4/2006 | Vic et al. |
| 2006/0104919 A1 | 5/2006 | Novak |
| 2006/0110334 A1 | 5/2006 | Rollat-Corvol |
| 2006/0110350 A1 | 5/2006 | Samain et al. |
| 2006/0115445 A1 | 6/2006 | Brun et al. |
| 2006/0179587 A1 | 8/2006 | Brun |
| 2006/0233731 A1 | 10/2006 | Vic et al. |
| 2006/0237696 A1 | 10/2006 | Gourlaouen et al. |
| 2006/0263315 A1 | 11/2006 | Plos et al. |
| 2007/0141002 A1 | 6/2007 | Montezinos et al. |
| 2007/0197704 A1 | 8/2007 | Walter et al. |
| 2007/0253927 A1 | 11/2007 | Jegou et al. |
| 2008/0038218 A1 | 2/2008 | Brun et al. |
| 2008/0066773 A1 | 3/2008 | Anderson et al. |
| 2008/0311053 A1 | 12/2008 | Curtis |
| 2010/0247463 A1 | 9/2010 | Yu et al. |
| 2013/0336913 A1 | 12/2013 | Anderson et al. |

FOREIGN PATENT DOCUMENTS

| | | |
|---|---|---|
| EP | 356271 B1 | 4/1995 |
| EP | 1787680 A2 | 5/2007 |
| EP | 2070514 A3 | 10/2009 |
| EP | 1958610 A3 | 4/2012 |
| FR | 2717177 B1 | 5/1996 |
| FR | 2899810 A1 | 10/2007 |
| FR | 2953712 B1 | 12/2012 |
| GB | 1311902 A | 3/1973 |
| GB | 1312675 A | 4/1973 |
| GB | 1318170 A | 5/1973 |
| JP | S4925334 B1 | 6/1974 |
| JP | H04-164908 | 6/1992 |
| JP | H08-048615 | 2/1996 |
| JP | H09-328414 | 12/1997 |
| JP | 2000-191603 | 11/2000 |
| JP | 2001199845 A | 7/2001 |
| JP | 3421433 B2 | 6/2003 |
| JP | 2005513087 A | 5/2005 |
| JP | 4925334 B2 | 4/2012 |
| RU | 2266300 C2 | 6/2004 |
| RU | 2246929 C2 | 8/2004 |
| WO | 93/16809 A2 | 9/1993 |
| WO | 9316684 A1 | 9/1993 |
| WO | 02051370 A1 | 7/2002 |
| WO | 02076412 A2 | 10/2002 |
| WO | 2007125236 A1 | 8/2007 |
| WO | 2007118812 A1 | 10/2007 |
| WO | 2010034924 A1 | 4/2010 |
| WO | 2015051733 A1 | 4/2015 |
| WO | 2015086678 A1 | 6/2015 |

OTHER PUBLICATIONS

Office Action in European Patent Application No. 08841660.7, dated Mar. 20, 2015.

Office Action in Canadian Patent Application No. 2,703,168, dated Feb. 23, 2015.

Fisher, J.P. et al., "Photoinitiated Polymerization of Biomaterials", Annu. Rev. Mater. Res., vol. 31, pp. 171-181, 2001.

"Best of Beauty", Allure magazine, pp. 214, 216, 218, 220, and 222, Oct. 2008.

Bottle label for "TruLift, Stop the Frizz, Anti-frizz Styling Cream for Thick to Coarse Hair," 4 fl. oz., 2009.

Print out entitled, "2009 Innovation Edison Best New Products of the Year," printed from http://www.edisonawards.com/09awards-nominees.hp, 2 pages, 2009.

(56) References Cited

OTHER PUBLICATIONS

Non-Final Office Action in U.S. Appl. No. 12/841,724, dated Nov. 8, 2011.
Final Office Action in U.S. Appl. No. 12/420,539, dated Mar. 24, 2010.
Non-Final Office Action in U.S. Appl. No. 12/420,539, dated Jan. 4, 2010.
Written Opinion in Singapore Appln. No. 201002038-6, dated Jul. 7, 2011.
Restriction Requirement in U.S. Appl. No. 12/404,193, dated Sep. 18, 2009.
Non-Final Office Action in U.S. Appl. No. 12/404,193, dated Jan. 4, 2010.
Notice of Allowance in U.S. Appl. No. 12/404,193, dated Jun. 25, 2010.
Non-Final Office Action in U.S. Appl. No. 12/147,397, dated Aug. 29, 2011.
Notice of Allowance in U.S. Appl. No. 12/147,397, dated Feb. 14, 2012.
Notice of Allowance in U.S. Appl. No. 12/420,539, dated Jun. 14, 2010.
Restriction Requirement in U.S. Appl. No. 12/420,539, dated Sep. 18, 2009.
Restriction Requirement in U.S. Appl. No. 12/841,486, dated Dec. 16, 2011.
Restriction Requirement in U.S. Appl. No. 12/841,724, dated Jul. 18, 2011.
International Preliminary Report on Patentability of PCT/US2008/080819, dated Dec. 29, 2008.
International Search Report of PCT/US2008/080819, dated Dec. 29, 2008.
Office Action in Indian Patent Application No. 2573/DELNP/2010, dated Mar. 30, 2015.
Sundari CS., et al., "Self-Assembly of a Peptide With a Tandem Repeat of the Aβ16-22 Sequence Linked by a β Turn-Promoting Dipeptide Sequence" Peptide Science, (2015) vol. 104, No. 6, pp. 790-803.
Office Action in European Patent Application No. 08841660.7, dated Nov. 13, 2015.
Written Opinion in Singapore Application No. 2012078523, dated Oct. 6, 2014.
Office Action in Russian Application No. 2010112584, dated Jun. 25, 2012, and its English translation.
Final Office Action of U.S. Appl. No. 12/841,724, dated May 9, 2012.
Non-Final Office Action of U.S. Appl. No. 12/841,486, dated Apr. 11, 2012.
Non-Final Office Action issued in U.S. Appl. No. 13/490,644, dated Apr. 10, 2013.
Non-Final Office Action issued in U.S. Appl. No. 12/841,724, dated Mar. 29, 2013.
"International Cosmetic Ingredient Dictionary of Handbook", The Cosmetic, Toiletry, and Fragrance Association, Washington, D.C., vol. 1, pp. 733-734, (2006).
Extended European Search Report of European Patent Application No. 0884166.7, dated Aug. 29, 2013.
Office Action in Japanese Application No. 2010-531208, dated Sep. 6, 2013, and its English translation.
Hayakawa, T., "Effect of Changing Molecular End Groups on Surface Properties: Synthesis and Characterization of Poly(styrene-b-semifluorinated isoprene) Block Copolymers with-CF2H End Groups" Macromolecules 2000, vol. 33, pp. 8012-8019.
Written Opinion in Singapore Patent Application No. 20121752-3, dated May 29, 2014.
Search Report for Singapore Patent Application No. 20121752-3, dated May 29, 2014.
Office Action in European Patent Application No. 08841660.7, dated Jun. 17, 2014.
Office Action in Canadian Patent Application No. 2,703,168, dated May 14, 2014.
Office Action in Japanese Application No. 2010-531208, dated Aug. 5, 2014, and its English translation.
Office Action in Korean Application No. 2010-7011157, dated Jan. 24, 2014, and its English translation.
Non-Final Office Action of U.S. Appl. No. 13/975,573, dated Oct. 22, 2014.
Notice of Allowance in Japanese Application No. 2010-531208, dated Jan. 13, 2015, and its English translation.
Restriction Requirement in U.S. Appl. No. 12/797,141, dated Jun. 22, 2011.
Non-Final Office Action in U.S. Appl. No. 12/797,141 dated Oct. 25, 2011.
Non-Final Office Action in U.S. Appl. No. 12/797,141 dated Mar. 28, 2013.
Examination Report in Australia App. No. 2008316856, dated May 21, 2012.
Final Office Action in U.S. Appl. No. 12/979,141, dated Jul. 11, 2012.
Examination Report of Singapore Application No. 201207852-3, dated Dec. 15, 2016.
Examination Report of European Application No. 08841660.7-1468, dated Apr. 6, 2017.
Hearing Notice in Indian Application No. 2573/DELNP/2010, dated Jul. 19, 2017.

\* cited by examiner

HAIR CARE COMPOSITIONS AND METHODS OF TREATING HAIR

This application is a divisional of U.S. application Ser. No. 12/797,141, filed Jun. 9, 2010, which is a continuation of PCT Application No. PCT/US2008/080819, filed Oct. 22, 2008, which is a continuation-in-part of U.S. application Ser. No. 12/147,397, filed Jun. 26, 2008, now U.S. Pat. No. 8,226,934, which claims the benefit of U.S. Provisional Application No. 60/981,625, filed Oct. 22, 2007 and U.S. Provisional Application No. 60/981,632, filed Oct. 22, 2007. The contents of all of the above-mentioned applications are incorporated herein by reference in their entirety.

BACKGROUND OF THE INVENTION

Field of the Invention

The present invention relates to compositions, kits and methods for treating hair. More particularly, the present invention includes compositions, kits and methods for treating hair using compounds described below, but without agents for effecting polymerization.

The present invention also provides novel compositions that allow for long-lasting moisture resistance, that are more repellant to dirt particles than natural hair while simultaneously leaving much less residue and producing long-lasting shine.

Background of the Invention

The hair care industry is a multi-billion dollar industry in the United States alone. The industry includes the development, production, and marketing of a large array of products for hair care, including shampoos, gels, mousses, lotions, sprays, conditioners, coloring products, pomades, serums, waxes, and repair products. Most of these products utilize pre-formed polymers developed to impart a desired characteristic upon application to a user's hair. For example, polymers are used to give hair shine, style hair, preserve hair style, give hair a desired texture or feel, enhance hair color, condition hair, dry hair so it sets quickly, straighten or smoothen hair, soften hair, strengthen hair, make hard-to-treat hair manageable, enhance optical properties, provide hold to hair, provide frizz control and/or to repair damaged hair.

Some of the above-identified beneficial attributes have been afforded in existing hair care products through use of compositions containing conditioning agents such as silicones or other polymers, which have a high affinity for keratin and especially for scalp hair. Such compounds include, but are not limited to silicones such as cyclomethicone, dimethiconol, dimethicone, cyclopentasiloxane, cyclomethicone, trimethylsiloxyphenyl, dimethiconol, cyclopentasiloxane dimethicone copolyol. However, the coating on keratin fibers, such as the hair, obtained with such compositions often has an unpleasant tacky feel and also may be readily lost via transfer, for example when a hand is passed through the hair. In addition, as a result of such transfer the hair may give the impression of being dirty, sticky or tacky. Also, the effects of the use of such silicone compounds and polymers is not long lasting as they are removed by shampooing the hair, thus making it necessary to repeat application of the compositions to the hair, for example, after rinsing, washing or shampooing.

Attempts have been made to treat hair with certain acrylate monomers and polymerize them in situ by free-radical polymerization. For example, U.S. Pat. No. 3,676,550 discloses use of certain acrylate and methacrylate compositions as hair treatments. Those compositions employ an "inert solvent" (which contains 10 to 90% water; the remainder being water-miscible organic solvent).

Unfortunately, compositions and methods that employ in situ free radical polymerization tend to degrade the hair, since harsh chemicals are involved. Another problem reported for such compositions and methods is that the chemicals employed irritate and/or are harmful to the hair and/or skin and leave the hair feeling harsh, as well as causing hair discoloration. Furthermore, many such hair treatments may involve reduction of hair prior to treatment, which causes additional hair damage.

One approach to avoid the harsh chemicals and/or conditions involved in in situ polymerization has been to avoid monomers that do not require such initiators, but rather employ monomers that readily polymerize in the presence of moisture (water). Accordingly, U.S. Pat. No. 5,082,010 shows that cyanoacrylates have been used as a treatment for hair. Cyanoacrylate monomers readily polymerize in the presence of moisture and are said to be "instant adhesives." "Crazy Glue" (2-cyano acrylate) is such an example. In addition, a medical glue, 2-octyl cyanoacrylate, is FDA approved for use as a wound adhesive for use in surgery. Contact with the moisture in the air, or from a biological fluid or tissue, is sufficient for polymerization of such cyanoacrylates.

Thus, existing hair care treatments suffer from numerous technical limitations. In addition to these technical limitations, there are functional limitations and drawbacks of using existing hair care formulations. One problem common to many hair care products is poor efficacy and longevity. For example, existing hair care treatments are not robust and can lose their efficacy over the course of a day. Many treatments lose their efficacy upon exposure to water or excess humidity. In addition, many hair treatments weigh down hair, flake off, leave unsightly residues, fail to dry and set quickly, do not provide adequate hold, and are not effective for hard-to-treat hair (e.g., naturally curly hair). Treatments have been developed which overcome some of these issues; however, they typically involve permanently treating the hair with reducing and/or oxidizing agents which can damage hair. Thus, there remains a need for hair treatments that withstand the rigors of a typical user's daily routine and maintain efficacy in a variety of environments without damaging hair fibers. It is preferable that a hair treatment be long lasting, not weigh down hair, not flake, and not leave any undesirable residues. Furthermore, the hair treatment should preferably dry and set relatively quickly, provide adequate hold, and be able to manage hard-to-treat hair.

SUMMARY OF THE INVENTION

As described herein, it has been discovered that certain organic chemical compounds, applied to hair, produce effects and characteristics desired by hair product consumers. The compounds are preferably not polymers such as those typically used in hair care products. The compounds are fluorinated but are not perfluorinated. In certain embodiments, a combination of compounds described herein are used to treat hair. The compositions, kits and methods of the present invention afford numerous beneficial effects that are especially desired for treating scalp hair, including: (1) controlling moisture penetration into the hair (frizz control), (2) providing a soft feel to the hair, without a harsh feeling (conditioning), (3) increasing the shine of the hair, (4) enhancing the hair's color, (5) avoiding the feeling of stickiness to the hair (and consequently resisting accumulation of dirt to the hair), (6) dries and sets quickly, (7) can help generate and or preserve the style of the hair, (8) adding strength to the hair, (9) leaving a low amount of residue (are "weightless"), (10) do not flake off the hair, (11) lasting over the course of more than one day, even more than 5 days, (12) affecting, including reducing, the surface energy of the hair (and thereby affording quicker drying of hair), (13) affording manageability for hard-to-treat hair, as well as repairing damaged hair, (14) providing hold, and (15) providing shape.

In one aspect, the invention is a method of treating scalp hair comprising the step of: applying to the hair a non-toxic composition comprising a non-perfluorinated, non-polymeric compound of formula (I) with a cosmetically acceptable excipient:

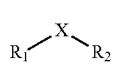
(I)

wherein X is selected from the group consisting of $CH_2$, $CHCH_3$, and $CCH_3CH_3$;

wherein $R_1$ and $R_2$ are independently selected from the group consisting of: hydrogen; cyclic or acyclic $C_1$-$C_{20}$ aliphatic; cyclic or acyclic $C_1$-$C_{20}$ heteroaliphatic; cyclic or acyclic $C_1$-$C_{20}$ acyl; $C_1$-$C_{20}$ aryl; $C_1$-$C_{20}$ heteroaryl; —OC(=O)R, wherein R is an alkenyl radical; —COOR$_4$; —C(=O)R$_4$; —OH; —NR$_B$R$_C$; and —CONR$_B$R$_C$, wherein R$_4$, R$_B$ and R$_C$ are independently selected from the group consisting of: hydrogen; cyclic or acyclic $C_1$-$C_{20}$ aliphatic; cyclic or acyclic $C_1$-$C_{20}$ heteroaliphatic; cyclic or acyclic $C_1$-$C_{20}$ acyl; $C_1$-$C_{20}$ aryl; and $C_1$-$C_{20}$ heteroaryl, which groups may be substituted or unsubstituted, and wherein $R_1$ and $R_2$ may be substituted or unsubstituted, provided that $R_1$ and $R_2$ taken together contain at least three carbon atoms; $R_1$ and $R_2$ taken together are substituted with a total of at least four fluorine atoms; and $R_1$ and $R_2$ taken together contain no more than one aromatic ring structure; and provided that the compound of formula (I) does not contain an Si—O bond; is not a polyether, a fluorinated acid, an oxyacetamide, or a carbonate.

In certain embodiments, at least one of $R_1$ and $R_2$ is substituted with —COOR$_4$, —C(=O)R$_4$, —OH, —NR$_B$R$_C$ or —CONR$_B$R$_C$, wherein R$_4$, R$_B$ and R$_C$ are independently selected from the group consisting of: hydrogen; cyclic or acyclic $C_1$-$C_{20}$ aliphatic; cyclic or acyclic $C_1$-$C_{20}$ heteroaliphatic; cyclic or acyclic $C_1$-$C_{20}$ acyl; $C_1$-$C_{20}$ aryl; and $C_1$-$C_{20}$ heteroaryl, which groups may be substituted or unsubstituted.

In another aspect, the non-perfluorinated, non-polymeric compound is applied to the hair with a cosmetically acceptable excipient to afford decreased moisture flux, which is a measure of moisture resistance. In another aspect, the non-perfluorinated, non-polymeric compound is applied to the hair with a cosmetically acceptable excipient to afford resistance to dirt. In another aspect, the non-perfluorinated, non-polymeric compound is applied to the hair with a cosmetically acceptable excipient to afford substantially less residue on the hair than other hair care products, which is a measure of weightlessness of the composition.

In certain embodiments, methods according to the invention do not employ a step consisting of rinsing the hair after applying the compound.

In certain embodiments, a composition containing a compound of formula (I) is applied to the hair under conditions such that there is no substantial polymerization of the compound.

In certain embodiments, the methods according to the invention do not employ a step of heating of the hair with a heating source that emits above about 160° C., and even more preferably without a step of heating the hair with a heating source that emits above about 120° C. after applying the non-toxic composition.

The present invention also provides kits for treating scalp hair comprising at least one non-toxic composition comprising a compound of formula (I) above, and instructions for use of the kit, wherein the instructions do not direct rinsing the hair, heating the hair, or use of polymerization initiator, as described above.

The invention also provides formulations of the fluorinated compound in inventive cosmetic hair care compositions including suitable excipients.

In the Examples used for testing and comparative testing herein, the compound is 2,2,3,3,4,4,5,5-octafluoropentyl methacrylate. "Hair Spray A" corresponds to Example 29, "Hair Spray B" corresponds to Example 30, "Hair Cream A" corresponds to Example 31, "Hair Cream B" corresponds to Example 32, "Hair Cream C" corresponds to Example 33, and "Hair Cream D" corresponds to Example 34.

In another aspect, the invention is a method of treating scalp hair comprising the step of applying a hair care composition so that the hair has decreased moisture flux. In certain embodiments, hair treated according to the method has at least 4 percent, at least 10 percent, at least 20 percent, at least 50 percent, or at least 80 percent decreased moisture flux.

Decreased moisture flux is measured according to the protocol described herein, and provides a measure of moisture resistance. Thus, the methods according to the invention may be used to reduce frizz.

In still another aspect, the method comprises applying to scalp hair a hair care composition that results in decreased weight gain. In embodiments, hair treated according to the method has no more than 15 percent, no more than 10 percent, no more than 7 percent, or no more than 5 percent weight gain. Weight gain is measured according to the protocol described herein and provides a measure of resistance to dirt accumulation. Hair that has less weight gain is more resistant to dirt.

In still another aspect, the invention is a method of treating hair comprising the step of applying a hair care composition that provides a greater feeling of weightlessness. Weightlessness may be characterized by the weight loss of the composition as measured by the protocol described herein. In embodiments according to the invention, the composition affords at least 25 percent, at least 50 percent, at least 70 percent, at least 80 percent or at least 90 percent weight loss.

The present invention also provides novel compositions that can be used to aid in the lubrication of hair to assist in shaving any part of the body, for example, the beard, the legs and the underarms.

BRIEF DESCRIPTION OF THE DRAWINGS

The features and advantages of the present invention will become more apparent from the detailed description set forth below when taken in conjunction with the drawings indicate identical or functionally similar elements.

DETAILED DESCRIPTION OF THE INVENTION

Figure 1:
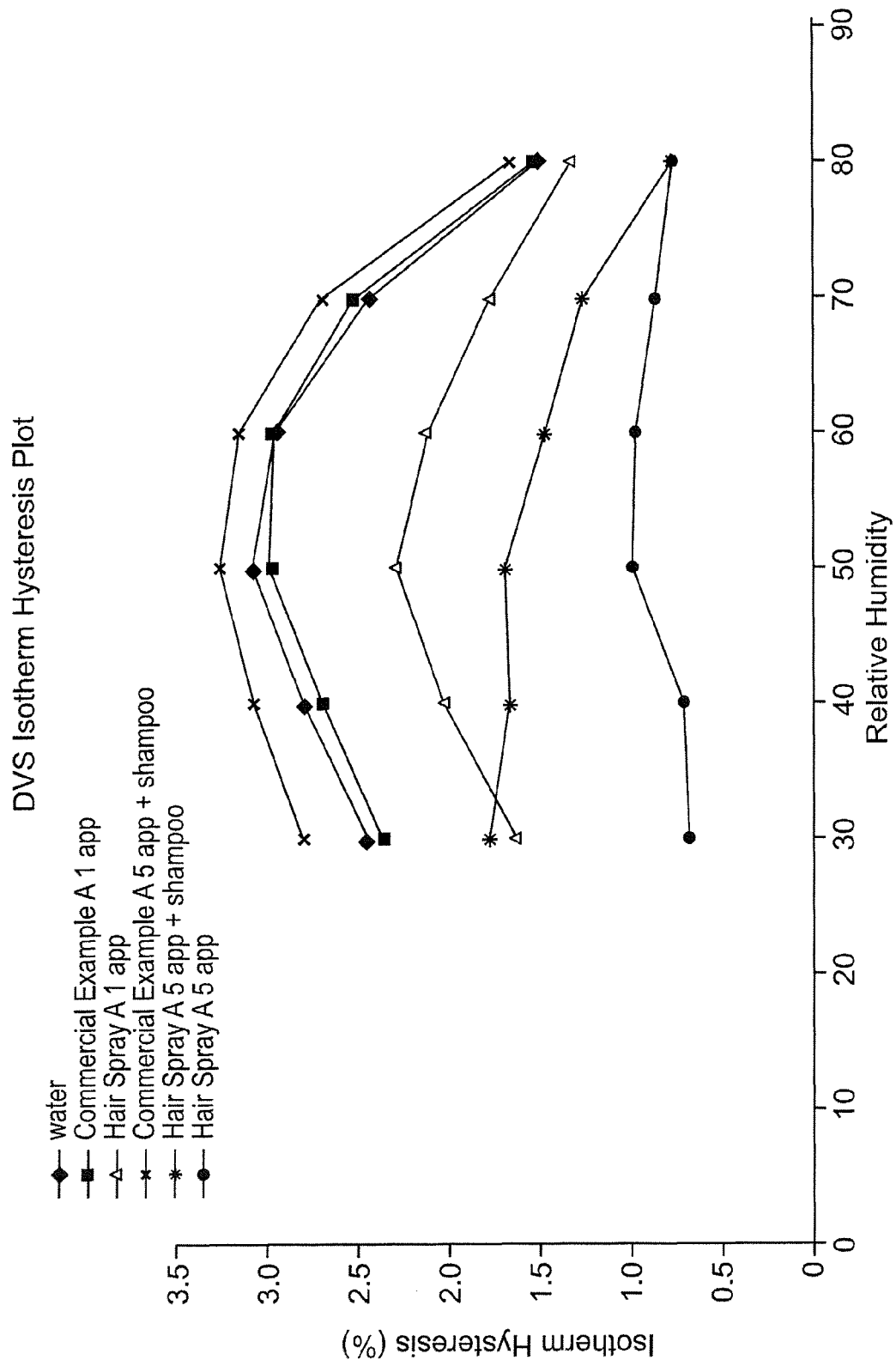
FIG. 1 is a plot showing DVS isotherm hysteresis for an embodiment according to the invention and competitor product compared to water.
Figure 2:
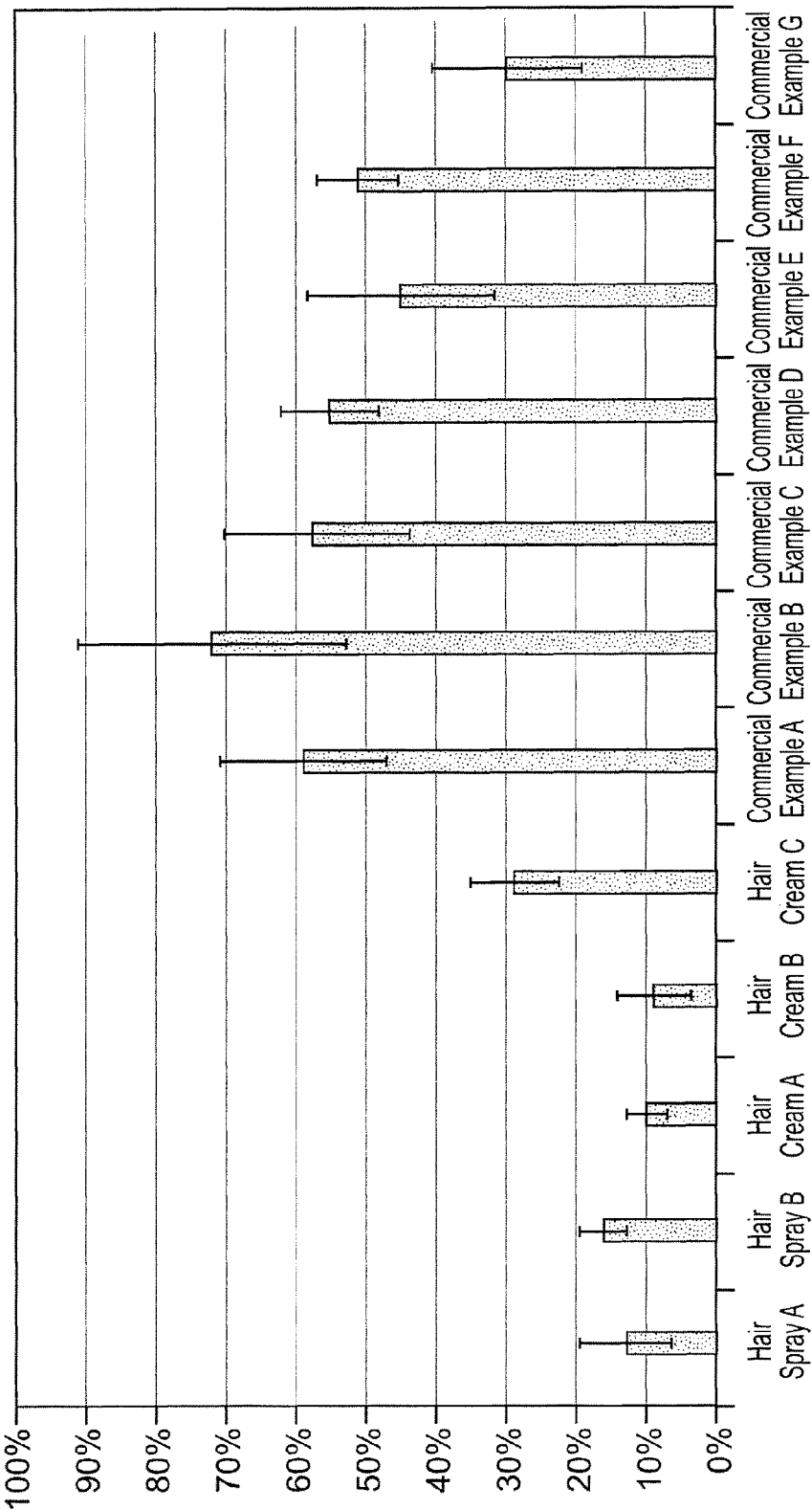
FIG. 2 shows the percent mass remaining after drying times of 10 and 30 minutes at 55° C. for sprays/serums and creams, respectively, for formulations according to the invention and competitor products when tested according to Weightless Test I.

In one aspect, the invention is a method of treating scalp hair comprising the step of applying to the hair a non-toxic composition comprising a non-perfluorinated, non-polymeric compound of formula (I)) with a cosmetically acceptable excipient:

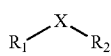
(I)

wherein X is selected from the group consisting of $CH_2$, $CHCH_3$, and $CCH_3CH_3$;

wherein $R_1$ and $R_2$ are independently selected from the group consisting of: hydrogen; cyclic or acyclic $C_1$-$C_{20}$ aliphatic; cyclic or acyclic $C_1$-$C_{20}$ heteroaliphatic; cyclic or acyclic $C_1$-$C_{20}$ acyl; $C_1$-$C_{20}$ aryl; $C_1$-$C_{20}$ heteroaryl; —OC(=O)R, wherein R is an alkenyl radical; —COOR$_A$; —C(=O)R$_A$; —OH; —NR$_B$R$_C$; and —CONR$_B$R$_C$, wherein $R_A$, $R_B$ and $R_C$ are independently selected from the group consisting of: hydrogen; cyclic or acyclic $C_1$-$C_{20}$ aliphatic; cyclic or acyclic $C_1$-$C_{20}$ heteroaliphatic; cyclic or acyclic $C_1$-$C_{20}$ acyl; $C_1$-$C_{20}$ aryl; and $C_1$-$C_{20}$ heteroaryl, which groups may be substituted or unsubstituted, and wherein $R_1$ and $R_2$ may be substituted or unsubstituted, provided that $R_1$ and $R_2$ taken together contain at least three carbon atoms; $R_1$ and $R_2$ taken together are substituted with a total of at least four fluorine atoms; and $R_1$ and $R_2$ taken together contain no more than one aromatic ring structure; and provided that the compound of formula (I) does not contain an Si—O bond; is not a polyether, a fluorinated acid, an oxyacetamide, or a carbonate.

$R_1$ and $R_2$ in formula (I) may have the same general definitions as $R_1'$ and $R_2'$ below.

In certain embodiments, one or both $R_1$ and $R_2$ may be substituted with 0, 1, or 2 substituents selected from the group consisting of alkyl, alkenyl, alkynyl, cyano, halo, formyl, nitro, hydroxy, alkoxy, —NH$_2$, —N(H)alkyl, —N(alkyl)$_2$, —C(=O)OH, —C(=O)Oalkyl, haloalkyl, hydroxyalkyl and alkoxyalkyl.

In embodiments, at least one of $R_1$ and $R_2$ is substituted with —COOR$_A$, —C(=O)R$_A$, —OH, —NR$_B$R$_C$ or —CONR$_B$R$_C$, wherein $R_A$, $R_B$ and $R_C$ are independently selected from the group consisting of: hydrogen; cyclic or acyclic $C_1$-$C_{20}$ aliphatic; cyclic or acyclic $C_1$-$C_{20}$ heteroaliphatic; cyclic or acyclic $C_1$-$C_{20}$ acyl; $C_1$-$C_{20}$ aryl; and $C_1$-$C_{20}$ heteroaryl, which groups may be substituted or unsubstituted.

For example, one or more of $R_A$ $R_B$ and $R_C$ may be substituted with 0, 1, or 2 substituents selected from the group consisting of alkyl, alkenyl, alkynyl, cyano, halo, formyl, nitro, hydroxy, alkoxy, —C(=O)OH, —C(=O)Oalkyl, haloalkyl, hydroxyalkyl and alkoxyalkyl.

In certain embodiments the hair is treated with a composition containing an acrylate or methacrylate compound according to Formula (I), wherein $R_1$ and $R_2$ are selected to yield a compound according to Formula (II):

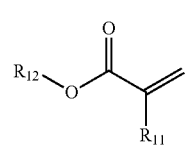
(II)

wherein $R_{11}$ is hydrogen or methyl optionally substituted with one or more fluorine; and $R_{12}$ is a radical selected from the group consisting of cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; and substituted or unsubstituted heteroaryl, wherein $R_{12}$ contains the "X" moiety of Formula (I).

The method of the present invention preferably does not employ a step of applying a composition containing more than about 0.1% weight/weight, more preferably, about 0.01% weight/weight, even more preferably, more than about 0.001% weight/weight of a free radical initiator selected from the group consisting of a heat-activated initiator that is activated at or above ambient temperature and an initiator that is active at ambient temperature.

The method of the present invention preferably does not further employ a step consisting of applying a composition containing more than about 0.1% weight/weight, preferably, more than about 0.01% weight/weight, and even more preferably, more than about 0.001% weight/weight of a uv-activated free radical initiator that is activated under ambient light.

In a certain embodiment, the method of the present invention preferably does not employ a step consisting of heating hair with a heating source that emits above about 160° C. and, even more preferably, above about 120° C., after applying the non-toxic composition.

In a preferred embodiment, $R_{12}$ of formula (I) above contains at least four fluorine atoms.

In a preferred embodiment, the compound of formula (I) above is selected from the group consisting of 2,2,3,3,4,4,5,5-octafluoro-1,6-hexyl dimethacrylate; 2,2,3,3,4,4,5,5-octafluoro-1,6-hexyl diacrylate; 1H,1H,11H-eicosafluoroundecyl acrylate; 1H,1H,11H-eicosafluoroundecyl methacrylate; 2,2,3,3,4,4,5,5-octafluoro-1,6-hexyldiacrylate; 2,2,3,3,4,4,5,5-octafluoro-1,6-hexyldimethacrylate; 2,2,3,3,4,4,5,5-octafluoropentyl methacrylate; 2,2,3,3,4,4,5,5-octafluoropentyl acrylate; 2,2,3,3,4,4-hexafluoro-1,5-pentyl diacrylate; 2,2,3,3,4,4-hexafluoro-1,5-pentyl dimethacrylate; 1H,1H,7H-dodecafluoroheptyl acrylate; and 1H,1H,7H-dodecafluoroheptyl methacrylate.

In a preferred embodiment, the compound of formula (I) is an octafluoropentyl methacrylate. Still more preferred, the compound according to formula I is:

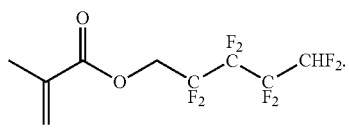 [SMILES: C=C(C)C(=O)OCC(F)(F)C(F)(F)C(F)(F)C(F)F]

The preferred embodiments in features described herein with respect to the non-toxic composition comprising a compound of formula (I) described above are all applicable to each individual compound described above. For example, the method of the present invention, wherein the method does not employ a step of applying a composition containing more than about 0.01% weight/weight of a free radical initiator selected from the group consisting of a heat-activated initiator that is activated at or above ambient temperature and an initiator that is active at ambient temperature, applies to each individual compound described above. For example, the method of the present invention wherein the method does not employ a step consisting of heating hair with a heating source that emits above about 120° C. after applying the non-toxic composition applies to each individual compound described above.

The present invention also provides a method of treating scalp hair comprising the step of applying to the hair a non-toxic composition comprising a compound of formula (I) described above, and wherein the method does not employ a step consisting of rinsing the hair after applying the compound. Preferably, the method does not employ a step consisting of rinsing the hair within at least 30 minutes to several hours, for example, about 1, 2, 3, or 4 hours after applying the compound.

The present invention also provides a method of treating scalp hair comprising the step of applying to the hair a non-toxic composition comprising a compound of formula (I) as described above under conditions wherein there is no substantial polymerization of the compound.

Yet another embodiment of the present invention provides a composition for treating hair comprising a compound of formula (I), or mixtures thereof, as the active ingredient with a cosmetically acceptable excipient. The fluorinated compound of formula (I), or mixtures thereof, may be provided in an amount of 0.001% to 20% (w/w) of the composition, preferably 0.01% to 10% (w/w), more preferably 0.1% to 5% (w/w) of the composition and most preferably in an amount of about 1% to about 3% (w/w) of the composition. This composition lacks substantial presence of a free radical initiator, a polymerization initiator or a polymerization catalyst that causes substantial polymerization.

The present invention also provides kits for use in treating hair based on the inventive hair care formulations. In another aspect, the present invention provides kits including the inventive cosmetic hair care compositions and instructions for using the composition in treating hair. The kit may include enough of the formulation for one use or multiple uses (e.g., approximately 2, 3, 4, 5, 10, 15, 20, 25, or 50). The kit may include any or all of the following components: hair care formulation, tube, bottle, spray bottle, brush, hair dryer, containers, and instructions for use. The formulations of the kit may be packaged as lotions, mousses, solutions, gels, pomades, serums, waxes, emulsions, suspensions, pumpable hair sprays, aerosol sprays, and non-aerosol sprays (e.g., atomisers). Hair care formulations are typically conveniently packaged in a suitable container for shipping and/or application of the composition. For example, a composition may be provided in a pump spray bottle or spray can. In certain embodiments, the kits are conveniently packaged for use by the end use along with instructions for use in accordance with the present invention. In certain embodiments, the kit is tailored for producing a desired characteristic in the treated hair. The kit may also include other hair care products including dyes, shampoos, conditioners, gels, mousses, pomades, serums, waxes, etc. The kit may also include all the materials needed for treating hair with the inventive hair care composition. The kit may include the materials conveniently packaged for use in a hair stylist's shop or for home use.

In certain embodiments, the instructions for use of the kit of the present invention do not direct heating hair with a heating source that emits above about 160° C., preferably above about 120° C., after applying the non-toxic composition; rinsing the hair within at least 30 minutes to several hours, for example, about 1, 2, 3, or 4 hours applying the compound. Preferably, the kit does not include instructions for applying a composition containing an effective amount of a polymerization initiator, such as a heat-activated initiator that is activated at or above ambient temperature, or an initiator that is active at ambient temperature. According to preferred embodiments, following the instructions provided with kits according to the invention results in no substantial polymerization of the compound.

There are many means for providing that no substantial polymerization of the monomer compound is occurring, including the addition of one or more polymerization inhibitors, the addition of one or more reducing agents, waiting for a sufficient period of time until there are no longer an appreciable number of free-radicals by virtue of them terminating, cooling the contents of the reactor to limit the reactivity of the free-radicals, and combinations thereof. A preferred means involves the addition of one or more polymerization inhibitors such as, for example, N,N-diethylhydroxylamine, N-nitrosodiphenylamine, 2,4-dinitrophenylhydrazine, p-phenylenediamine, phenathiazine, alloocimene, triethyl phosphite, 4-nitrosophenol, 2-nitrophenol, p-aminophenol, 4-hydroxy-TEMPO (also known as 4-hydroxy-2,2,6,6, tetramethylpiperidinyloxy, free radical), hydroquinone, p-methoxyhydroquinone, tert-butyl-p-hydroquinone, 2,5-di-tert-butyl-p-hydroquinone, 1,4-naphthalenediol, 4-tert butyl catechol, copper sulfate, copper nitrate, cresol and phenol. When used, the polymerization inhibitors or reducing agents are added in effective amount to substantially stop any polymerization, generally from 25 to 5,000 parts per million ("ppm"), preferably from 50 to 3,500 ppm based on polymer solids.

According to certain embodiments, the present invention provides a method of treating scalp hair wherein the compound of formula (I) is an ester having the structure

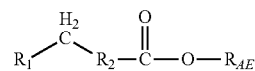

wherein $R_1$ and $R_2$ are as defined herein, and wherein $R_{AE}$ is defined as for $R_A$; except that $R_{AE}$ is not hydrogen.

According to certain embodiments, the present invention also provides a method of treating scalp hair wherein the compound of formula (I) is an alcohol having the structure

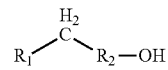

wherein $R_1$ and $R_2$ are as defined herein.

In other embodiments, compositions according to the invention may contain an ether having the structure

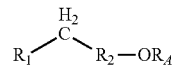

wherein $R_1$, $R_2$ and $R_4$ are as defined herein. Thus, formula (I) may be defined so that $R_1$ and $R_2$ independently may be, or may be substituted with, $-OR_A$, wherein $R_A$ is selected from the group consisting of cyclic or acyclic $C_1$-$C_{20}$ aliphatic; cyclic or acyclic $C_1$-$C_{20}$ heteroaliphatic; cyclic or acyclic $C_1$-$C_{20}$ acyl; $C_1$-$C_{20}$ aryl and $C_1$-$C_{20}$ hetero aliphatic, any of which groups may be substituted or unsubstituted. When the compound according to Formula (I) is an ether containing a single ether oxygen, then the compound has a viscosity greater than 5 mPa at 25° C., optionally greater than 10 mPa and optionally greater than 20 mPa at 25° C. In preferred embodiments, the ether compound is not a solvent for another fluorine containing active compound in the composition.

Similarly, according to preferred embodiments, the composition according to the invention does not include a compound containing two or more ether moieties (characterized by an oxygen bonded between two adjacent carbon groups).

According to certain embodiments, the present invention also provides a method of treating scalp hair wherein the compound of formula (I) is an amine having the structure

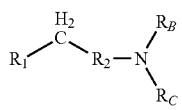

wherein $R_1$, $R_2$, $R_B$ and $R_C$ are as defined herein.

According to certain embodiments, the present invention also provides a method of treating scalp hair wherein the compound of formula (I) is an amide having the structure

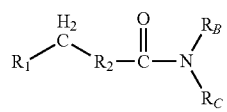

wherein $R_1$, $R_2$, $R_B$ and $R_C$ are as defined herein.

Definitions of specific functional groups and chemical terms are described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito: 1999, the entire contents of which are incorporated herein by reference.

Certain compounds of the present invention may exist in particular geometric or stereoisomeric forms. The present invention contemplates all such compounds, including cis- and trans-isomers, E- and Z-isomers, R- and S-enantiomers, diastereomers, (d)-isomers, (l)-isomers, (−)- and (+)-isomers, racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term acyl as used herein refers to a group having the general formula —C(O)R, where R is alkyl, alkenyl, alkynyl, aryl, carbocyclic, heterocyclic, or aromatic heterocyclic. An example of an acyl group is acetyl.

The term aliphatic, as used herein, includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "lower alkyl" is used to indicate those alkyl groups (cyclic, acyclic, substituted, unsubstituted, branched or unbranched) having 1-6 carbon atoms.

The term alkyl as used herein refers to saturated, straight- or branched-chain hydrocarbon radicals derived from a hydrocarbon moiety containing between one and twenty carbon atoms by removal of a single hydrogen atom. In some embodiments, the alkyl group employed in the invention contains 1-10 carbon atoms. In another embodiment, the alkyl group employed contains 1-8 carbon atoms. In still other embodiments, the alkyl group contains 1-6 carbon atoms. In yet another embodiments, the alkyl group contains 1-4 carbons. Examples of alkyl radicals include, but are not limited to, methyl, ethyl, n-propyl, isopropyl, n-butyl, isobutyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like, which may bear one or more substituents.

The term alkoxy as used herein refers to a saturated (i.e., alkyl-O—) or unsaturated (i.e., alkenyl-O— and alkynyl-O—) group attached to the parent molecular moiety through an oxygen atom. In certain embodiments, the alkyl group contains 1-20 aliphatic carbon atoms. In certain other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples include, but are not limited to, methoxy, ethoxy, propoxy, isopropoxy, n-butoxy, tert-butoxy, i-butoxy, sec-butoxy, neopentoxy, n-hexoxy, and the like.

The term alkenyl denotes a monovalent group derived from a hydrocarbon moiety having at least one carbon-carbon double bond by the removal of a single hydrogen atom. In certain embodiments, the alkenyl group employed in the invention contains 1-20 carbon atoms. In some embodiments, the alkenyl group employed in the invention contains 1-10 carbon atoms. In another embodiment, the alkenyl group employed contains 1-8 carbon atoms. In still other embodiments, the alkenyl group contains 1-6 carbon atoms. In yet another embodiments, the alkenyl group contains 1-4 carbons. Alkenyl groups include, for example, ethenyl, propenyl, butenyl, 1-methyl-2-buten-1-yl, and the like.

The term alkynyl as used herein refers to a monovalent group derived from a hydrocarbon having at least one carbon-carbon triple bond by the removal of a single hydrogen atom. In certain embodiments, the alkynyl group employed in the invention contains 1-20 carbon atoms. In some embodiments, the alkynyl group employed in the invention contains 1-10 carbon atoms. In another embodiment, the alkynyl group employed contains 1-8 carbon atoms. In still other embodiments, the alkynyl group contains 1-6 carbon atoms. Representative alkynyl groups include, but are not limited to, ethynyl, 2-propynyl (propargyl), 1-propynyl, and the like.

The term alkylamino, dialkylamino, and trialkylamino as used herein refers to one, two, or three, respectively, alkyl groups, as previously defined, attached to the parent molecular moiety through a nitrogen atom. The term alkylamino refers to a group having the structure —NHR' wherein R' is an alkyl group, as previously defined; and the term dialkylamino refers to a group having the structure —NR'R", wherein R' and R" are each independently selected from the group consisting of alkyl groups. The term trialkylamino refers to a group having the structure —NR'R"R'", wherein R', R", and R'" are each independently selected from the group consisting of alkyl groups. In certain embodiments, the alkyl group contain 1-20 aliphatic carbon atoms. In certain other embodiments, the alkyl group contains 1-10 aliphatic carbon atoms. In yet other embodiments, the alkyl group contains 1-8 aliphatic carbon atoms. In still other embodiments, the alkyl group contain 1-6 aliphatic carbon atoms. In yet other embodiments, the alkyl group contain 1-4 aliphatic carbon atoms. Additionally, R', R", and/or R'" taken together may optionally be —(CH$_2$)$_k$— where k is an integer from 2 to 6. Examples include, but are not limited to, methylamino, dimethylamino, ethylamino, diethylamino, diethylaminocarbonyl, methylethylamino, iso-propylamino, piperidino, trimethylamino, and propylamino.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups contain 1-8 aliphatic carbon atoms. In still other embodiments, the alkyl, alkenyl, and alkynyl groups contain 1-6 aliphatic carbon atoms. In yet other embodiments, the alkyl, alkenyl, and alkynyl groups contain 1-4 aliphatic carbon atoms. Examples of thioalkoxyl moieties include, but are not limited to, methylthio, ethylthio, propylthio, isopropylthio, n-butylthio, and the like.

Some examples of substituents of the above-described aliphatic (and other) moieties of compounds of the invention include, but are not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; F; Cl; Br; I; —OH; —NO$_2$; —CN; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

In general, the terms aryl and heteroaryl, as used herein, refer to stable mono- or polycyclic, heterocyclic, polycyclic, and polyheterocyclic unsaturated moieties having preferably 3-14 carbon atoms, each of which may be substituted or unsubstituted. Substituents include, but are not limited to, any of the previously mentioned substituents, i.e., the substituents recited for aliphatic moieties, or for other moieties as disclosed herein, resulting in the formation of a stable compound. In certain embodiments of the present invention, aryl refers to a mono- or bicyclic carbocyclic ring system having one or two aromatic rings including, but not limited to, phenyl, naphthyl, tetrahydronaphthyl, indanyl, indenyl, and the like. In certain embodiments of the present invention, the term heteroaryl, as used herein, refers to a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups can be unsubstituted or substituted, wherein substitution includes replacement of one, two, three, or more of the hydrogen atoms thereon independently with any one or more of the following moieties including, but not limited to: aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term carboxylic acid as used herein refers to a group of formula —$CO_2H$.

The terms halo and halogen as used herein refer to an atom selected from fluorine, chlorine, bromine, and iodine.

The term haloalkyl denotes an alkyl group, as defined above, having one, two, or three halogen atoms attached thereto and is exemplified by such groups as chloromethyl, bromoethyl, trifluoromethyl, and the like.

The term heteroaliphatic, as used herein, refers to aliphatic moieties that contain one or more oxygen, sulfur, nitrogen, phosphorus, or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$, wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term heterocyclic, as used herein, refers to an aromatic or non-aromatic, partially unsaturated or fully saturated, 3- to 10-membered ring system, which includes single rings of 3 to 8 atoms in size and bi- and tri-cyclic ring systems which may include aromatic five- or six-membered aryl or aromatic heterocyclic groups fused to a non-aromatic ring. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring.

The term aromatic heterocyclic, as used herein, refers to a cyclic aromatic radical having from five to ten ring atoms of which one ring atom is selected from sulfur, oxygen, and nitrogen; zero, one, or two ring atoms are additional heteroatoms independently selected from sulfur, oxygen, and nitrogen; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like. Aromatic heterocyclic groups can be unsubstituted or substituted with substituents selected from the group consisting of branched and unbranched alkyl, alkenyl, alkynyl, haloalkyl, alkoxy, thioalkoxy, amino, alkylamino, dialkylamino, trialkylamino, acylamino, cyano, hydroxy, halo, mercapto, nitro, carboxyaldehyde, carboxy, alkoxycarbonyl, and carboxamide.

Specific heterocyclic and aromatic heterocyclic groups that may be included in the compounds of the invention include radicals derived from: 3-methyl-4-(3-methylphenyl) piperazine, 3-methylpiperidine, 4-(bis-(4-fluorophenyl) methyl)piperazine, 4-(diphenylmethyl)piperazine, 4-(ethoxycarbonyl)piperazine, 4-(ethoxycarbonylmethyl) piperazine, 4-(phenylmethyl)piperazine, 4-(1-phenylethyl) piperazine, 4-(1,1-dimethylethoxycarbonyl)piperazine, 4-(2-(bis-(2-propenyl) amino)ethyl)piperazine, 4-(2-(diethylamino)ethyl)piperazine, 4-(2-chlorophenyl)piperazine, 4-(2-cyanophenyl)piperazine, 4-(2-ethoxyphenyl)piperazine, 4-(2-ethylphenyl)piperazine, 4-(2-fluorophenyl)piperazine, 4-(2-hydroxyethyl)piperazine, 4-(2-methoxyethyl) piperazine, 4-(2-methoxyphenyl)piperazine, 4-(2-methylphenyl)piperazine, 4-(2-methylthiophenyl) piperazine, 4-(2-nitrophenyl)piperazine, 4-(2-nitrophenyl) piperazine, 4-(2-phenylethyl)piperazine, 4-(2-pyridyl) piperazine, 4-(2-pyrimidinyl)piperazine, 4-(2,3-dimethylphenyl)piperazine, 4-(2,4-difluorophenyl) piperazine, 4-(2,4-dimethoxyphenyl)piperazine, 4-(2,4-dimethylphenyl)piperazine, 4-(2,5-dimethylphenyl) piperazine, 4-(2,6-dimethylphenyl)piperazine, 4-(3-chlorophenyl)piperazine, 4-(3-methylphenyl)piperazine, 4-(3,4-dichlorophenyl)piperazine, 4-3,4-dimethoxyphenyl) piperazine, 4-(3,4-dimethylphenyl)piperazine, 4-(3,4-methylenedioxyphenyl)piperazine, 4-(3,4,5-trimethoxyphenyl) piperazine, 4-(3,5-dichlorophenyl)piperazine, 4-(3,5-dimethoxyphenyl)piperazine, 4-(4-(phenylmethoxy)phenyl) piperazine, 4-(4-(3,1-dimethylethyl)phenylmethyl) piperazine, 4-(4-chlorophenyl)-3-methylpiperazine, 4-(4-chlorophenyl)piperazine, 4-(4-chlorophenyl)piperazine, 4-(4-chlorophenylmethyl)piperazine, 4-(4-fluorophenyl) piperazine, 4-(4-methoxyphenyl)piperazine, 4-(4-methylphenyl)piperazine, 4-(4-nitrophenyl)piperazine, 4-cyclohexylpiperazine, 4-ethylpiperazine, 4-hydroxy-4-(4-chlorophenyl)methylpiperidine, 4-hydroxy-4-phenylpiperidine, 4-hydroxypyrrolidine, 4-methylpiperazine, 4-phenylpiperazine, 4-piperidinylpiperazine, 4-(2-furanyl)carbonyl)piperazine, 4-((1,3-dioxolan-5-yl)methyl)piperazine, 6-fluoro-1,2,3,4-tetrahydro-2-methylquinoline, 1,4-diazacylcloheptane, 2,3-dihydroindolyl, 3,3-dimethylpiperidine, 4,4-ethylenedioxypiperidine, 1,2,3, 4-tetrahydroisoquinoline, 1,2,3,4-tetrahydroquinoline, azacyclooctane, decahydroquinoline, piperazine, piperidine, pyrrolidine, thiomorpholine, and triazole.

Notwithstanding the foregoing, according to preferred embodiments, compositions for treating hair according to the invention do not include compounds that have more than one aromatic ring structure. Preferably, the compounds do not contain fused aromatic rings.

The term carbamoyl, as used herein, refers to an amide group of the formula —CONH$_2$.

The term carbonyldioxyl, as used herein, refers to a carbonate group of the formula —O—CO—OR.

The term hydrocarbon, as used herein, refers to any chemical group comprising hydrogen and carbon. The hydrocarbon may be substituted or unsubstituted. The hydrocarbon may be unsaturated, saturated, branched, unbranched, cyclic, polycyclic, or heterocyclic. Illustrative hydrocarbons include, for example, methyl, ethyl, n-propyl, iso-propyl, cyclopropyl, allyl, vinyl, n-butyl, tert-butyl, ethynyl, cyclohexyl, methoxy, diethylamino, and the like. As would be known to one skilled in this art, all valencies must be satisfied in making any substitutions.

The terms substituted, whether preceded by the term "optionally" or not, and substituent, as used herein, refer to the ability, as appreciated by one skilled in this art, to change one functional group for another functional group provided that the valency of all atoms is maintained. When more than one position in any given structure may be substituted with more than one substituent selected from a specified group, the substituent may be either the same or different at every position. The substituents may also be further substituted (e.g., an aryl group substituent may have another substituent off it, such as another aryl group, which is further substituted with fluorine at one or more positions).

The term thiohydroxyl or thiol, as used herein, refers to a group of the formula —SH.

As used herein, a compound is perfluorinated if it contains a moiety in which every available hydrogen is replaced with fluorine. Thus, a compound that contains a trifluoromethyl group is perfluorinated and cannot be considered non-perfluorinated. A compound in which every available hydrogen is substituted with fluorine is perfluorinated, and cannot be considered non-perfluorinated, whether or not the compound contains a methyl group.

As used herein, the singular forms "a", "an", and "the" include the plural reference unless the context clearly indicates otherwise. Thus, for example, a reference to "a monomer" includes a plurality of such monomers.

"Animal": The term animal, as used herein, refers to humans as well as non-human animals, including, for example, mammals, birds, reptiles, amphibians, and fish. Preferably, the non-human animal is a mammal (e.g., a rodent, a mouse, a rat, a rabbit, a monkey, a dog, a cat, a primate, or a pig). An animal may be a domesticated animal. In certain embodiments, the animal is human. An animal may be a transgenic animal.

"Biocompatible": The term "biocompatible", as used herein is intended to describe compounds that are not toxic to cells. Compounds are "biocompatible" if their addition to cells in vitro results in less than or equal to 20% cell death. The administration in vivo does not cause inflammation, cancer, birth defects, neurotoxicity, or other such adverse side effects.

"Biodegradable": As used herein, "biodegradable" compounds are those that, when introduced into cells, are broken down by the cellular machinery or by hydrolysis into components that the cells can either reuse or dispose of without significant toxic effect on the cells (i.e., fewer than about 20% of the cells are killed when the components are added to cells in vitro). The components preferably does not cause inflammation, cancer, birth defects, neurotoxicity, or other such adverse side effects in vivo. In certain preferred embodiments, the chemical reactions relied upon to break down the biodegradable compounds are uncatalyzed. For example, the inventive materials may be broken down in part by the hydrolysis of the ester bonds found in cross-linked material.

"Keratin": The term "keratin" as used herein refers any one of a class of fibrous structural proteins found in hair, wool, and nails. Keratin proteins contains a large quantity of cysteine residues. Human hair is approximately 15% cysteine residues cross-linked by disulfide bridges. The helical keratin molecules twist around each other to form elongated strands call intermediate filaments.

"Monomer": As used herein, a "monomer" is a chemical compound that is capable of being linked to other monomers covalently to form a polymer. Examples of monomers include acrylates, methacrylates, epoxide containing compounds, styrenes, and vinyl alcohol. In certain embodiments, the monomers useful in accordance with the present invention are susceptible to free radical polymerization.

"Oligomer": The term "oligomer," as used herein, refers to a chemical compound with a finite number of structural units connected by covalent bonds. An oligomer has less monomeric units than the corresponding polymer. An oligomer has at least 3 and typically up to 100 monomeric units making up its structure.

"Peptide" or "protein": As used herein, a "peptide" or "protein" comprises a string of at least three amino acids linked together by peptide bonds. The terms "protein" and "peptide" may be used interchangeably. Peptide may refer to an individual peptide or a collection of peptides. Inventive peptides preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification, etc. In a preferred embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

"Polymer": The term "polymer," as used herein, refers to a chemical compound of repeating structural units (monomers) connected by covalent bonds. A polymer is typically of high molecular weight and may comprise 10s to 100s to 1000s or even more monomers. An aliphatic group such as $C_{20}$ with multiple methylene groups is not considered to be a polymer.

Active Hair Care Ingredients

A variety of active hair care ingredients may be used in the inventive cosmetic hair care compositions comprising fluorinated small organic molecules. Combinations of compounds may be used to treat hair, thereby creating different cosmetic effects. The availability of a wide range of compounds also allows for treating hair to achieve various desired properties, including the desirable effects on a subject's hair referred to above.

In preferred embodiments, the inventive compositions and methods afford the benefits of silicone containing composition without many of their drawbacks. Accordingly, the compositions, methods of the invention preferably do not employ any silicone compound (i.e., containing an Si—O bond); preferably the compositions and methods employ less than 10% wt/vol of such a silicone compound, preferably less than 1% wt/vol of such a silicone compound, more preferably below 0.5% wt/vol, more preferably below 0.2% wt/vol; more preferably below 0.1% wt/vol; more preferably below 0.05% wt/vol; more preferably below 0.01% wt/vol; and still more preferably below 0.001% wt/vol.

Preferred compounds employed in the inventive compositions and methods are not toxic, are not harmful to the hair or skin and do not leave the hair feeling harsh or cause hair discoloration, in contrast to in situ polymerizing compositions for example. Moreover, the preferred inventive compositions and methods do not rely on free-radical polymerization agents or pre- or post-treatment of the hair with either a reducing or oxidizing agent. In certain embodiments, the inventive compositions and methods do not employ a free radical initiator, a polymerization initiator or a polymerization catalyst. In certain embodiments, the inventive compositions and methods do not employ more than about 0.001% weight/weight, more preferably not more than about 0.01% weight/weight, even more preferably not more than about 0.1% weight/weight of a free radical initiator, a polymerization initiator or a polymerization catalyst. In certain embodiments, there is not more than approximately 0.001 per mol of a free radical initiator, a polymerization initiator or a polymerization catalyst per mol of monomer. Accordingly, the inventive compositions and methods preferably do not employ more than about 0.001% weight/weight, more preferably not more than about 0.01% weight/weight, even more preferably not more than about 0.1% weight/weight of a peroxide; a peracid, a peroxide generating system; a peroxomonosulfate; a peroxodisulfate; a diazo compound, a redox catalyst (such as $NH_4S_2O_8/NaHSO_3$; $H_2O/Fe^{3+}$; $S_2O_8^{-2}/RSH$; $Fe^{3+}/HSO_3^-$; $Ce^{+4}/ROH$; $KMnO_4$/citric acid; sodium sulfite).

In contrast to certain cyano acrylates, preferred compositions of the present invention employ monomers that do not readily polymerize simply by exposing the monomer to moisture, such as by contact of the monomer with moisture from a biological fluid or tissue as for cyanoacrylates. Indeed, the monomers of the present invention may be formulated as stable compositions using aqueous carriers, for example containing greater than 90% water as carrier. The monomers of the present inventions are not cyanoacrylates.

Use of the inventive compositions is simple and easy. Preferably, the inventive composition is applied to hair that has been just washed. It is not necessary to completely dry the hair, but rather, the hair may be towel dried, allowing for the hair to remain moist, or even dripping wet. A composition of the invention is applied and worked into the hair for example, by the use of a comb or brush, after which the hair is blow dried, preferably using heat from a conventional hair drier, even more preferably, using a heat source that emits below 160° C. and even more preferably, using a heat source that emits below 120° C. In the case of a composition that is a cream, it is recommended that the cream be worked into the ends of the hair, after which the composition is worked into the remaining length of the hair. It is not necessary, and indeed it is preferable, that there be no rinsing step after application of the inventive composition to the hair.

The compounds useful in accordance with the invention are typically low molecular weight organic compounds. In certain embodiments, the chemical compounds are not oligomeric or polymeric. That is, the compound is not an oligomer or low molecular weight polymer. In certain embodiments, the compounds are not peptides or proteins. In certain embodiments, the compounds are not oligonucleotides. In certain embodiments, the compounds are not biomolecules (i.e., compounds found in nature). In certain embodiments, the compounds are dimers. In certain other embodiments, the compounds are trimers.

The molecular weight of the compound used to treat hair is typically sufficient to prevent substantial evaporation of the compound from the treated hair without leaving residue from an excipient. This has the result that the composition has a "weightless" quality, which can be quantified as described herein. In certain embodiments, the molecular weight of the compound may be less than about 3,000 g/mol, less than about 2,500 g/mol, less than about 2,000 g/mol, less than about 1,500 g/mol, less than about 1,000 g/mol, less than about 500 g/mol, or less than about 400 g/mol.

In embodiments, the molecular weight of the compound ranges from about 50 g/mol to about 500 g/mol, 100 g/mol to about 500 g/mol, 100 g/mol to about 1,000 g/mol, 200 g/mol to about 1,000 g/mol, 500 g/mol to about 1,000 g/mol, or 1,000 g/mol to about 2,000 g/mol.

The compound typically has a boiling point greater than 50° C. In certain embodiments, the boiling point of the compound is greater than 55° C., greater than 60° C., greater than 65° C., greater than 70° C., greater than 75° C., greater than 80° C., greater than 85° C., greater than 90° C., greater than 95° C., greater than 100 C, greater than 110° C., greater than 120° C., greater than 130° C., greater than 140° C., greater than 150° C., greater than 175° C., or greater than 200° C.

The compound typically has a melting point less than 40° C. In certain embodiments, the melting point of the compound is less than 35° C., less than 30° C., less than 35° C., less than 30° C., less than 25° C., less than 20° C., less than 15 C, less than 10 C, or less than 0° C.

In certain embodiments, the compound has a melting point less than about 10° C. and a boiling point greater than about 60° C.; a melting point less than about 20° C. and a boiling point greater than about 70° C.; a melting point less than about 20° C. and a boiling point greater than about 80° C.; a melting point less than about 10° C. and a boiling point greater than about 100° C.; or a melting point less than about 20° C. and a boiling point greater than about 100° C.

In a certain embodiment, the compound comprises an unsaturated functional group such as a double or triple bond. Example of unsaturated functional groups include alkenes, alkynes, carbonyls, and imines. In certain embodiments, the compound includes a conjugated unsaturated system, an $\alpha,\beta$-unsaturated carbonyl moiety, an acrylate moiety, a crotonate moiety, a methacrylate moiety, a 2-fluoroacrylate moiety, a diacrylate moiety, a dicrotonate moiety, or a dimethacrylate moiety. In certain embodiments, the compound includes an alkene, a vinyl group, an allyl group, a diene or conjugated diene moiety. In certain embodiments, the compound includes an alkyne. In certain embodiments, the compound includes an eneyne moiety. In certain embodiments, the compound includes an aryl, phenyl or styrene moiety. In certain embodiments, the compound includes a heteroaryl moiety.

In a certain embodiment, useful compounds in the inventive hair care system include alkene-containing groups. In certain particular embodiments, the alkene is monosubstituted. In other embodiments, the alkene is disubstituted. Disubstituted alkenes may be either in the cis or trans configuration, or any mixture thereof. In yet other embodiments, the alkene is trisubstituted. The trisubstituted alkene may be in either the E or Z configuration, or any mixture thereof. In still other embodiments, the alkene is tetrasubstituted. Again, various isomers are possible and are considered part of this invention.

Thus, the compounds may be defined according to one of the formulae:

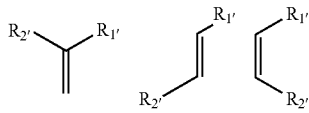

wherein $R_{1'}$ and $R_{2'}$ are each independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; $—OR_{A'}$; $—C(O)R_{A'}$; $—CO_2R_{A'}$; $—C(O)N(R_{A'})_2$; $—SR_{A'}$; $—SOR_{A'}$; $—SO_2R_{A'}$; $—NR_{A'}$; $—N(R_{A'})_2$; $—NHC(O)R_{A'}$; and $—C(R_{A'})_3$; and wherein each occurrence of $R_{A'}$ is independently selected from a group consisting of hydrogen, cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; alkoxy; aryloxy; alkylthio; arylthio; amino; alkylamino; dialkylamino; heteroaryloxy; heteroarylthio and a protecting group; or $R_{1'}$ and $R_{2'}$ form a cyclic structure; and provided that when $R_{1'}$ is hydrogen, $R_{2'}$ is not hydrogen with the proviso that one of $R_{1'}$ and $R_{2'}$ contains the methylene moiety described in connection with Formula (I).

In a preferred embodiment, $R_{1'}$ or $R_{2'}$ do not constitute a cyano acrylate moiety.

In a preferred embodiment, $R_{1'}$ or $R_{2'}$ form an acrylate where the moiety of the acrylate ester is not perfluorinated.

In other embodiments, $R_{1'}$ is a substituted or unsubstituted, branched or unbranched aliphatic moiety. In certain embodiments, $R_{1'}$ is an alkyl moiety. In certain embodiments, $R_{1'}$ is $C_1$-$C_6$ alkyl moiety. In certain embodiments, $R_{1'}$ is of one of the formulae:

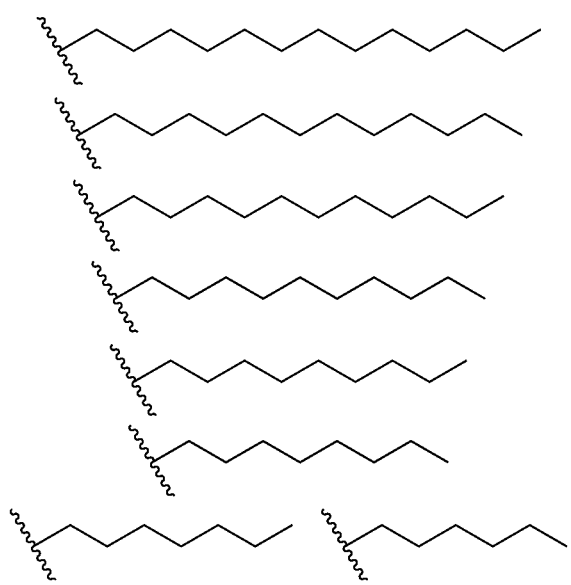

As would be appreciated by one of skill in this art, any of the above alkyl groups may be substituted, branched, unsaturated, and/or cyclic.

In certain particular embodiments, $R_{1'}$ is of the formula:

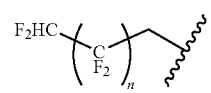

wherein n is an integer between 0 and 20, inclusive. In certain embodiments, n is an integer between 0 and 12, inclusive. In certain embodiments, n is an integer between 0 and 6, inclusive. In certain embodiments, n is an integer between 1 and 6, inclusive. In certain embodiments, n is an integer between 3 and 20, inclusive.

In certain embodiments, $R_{1'}$ is of the formula:

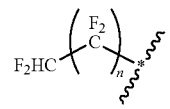

wherein n is an integer between 0 and 20, inclusive. In certain embodiments, n is an integer between 0 and 12, inclusive. In certain embodiments, n is an integer between 0 and 6, inclusive. In certain embodiments, n is an integer between 1 and 6, inclusive. In certain embodiments, n is an integer between 3 and 20, inclusive.

In yet other embodiments, $R_{1'}$ is a substituted or unsubstituted, branched or unbranched heteroaliphatic moiety. In still other embodiments, $R_{1'}$ is a substituted or unsubstituted acyl moiety.

In other embodiments, $R_{1'}$ is a substituted or unsubstituted aryl moiety. In certain particular embodiments, $R_{1'}$ is of the formula:

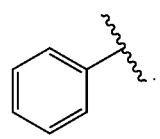 [SMILES: *c1ccccc1]

In certain particular embodiments, $R_{1'}$ is of the formula:

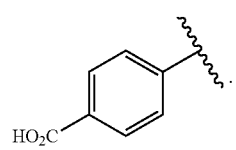

In certain particular embodiments, $R_{1'}$ is a substituted or unsubstituted phenyl moiety. In certain embodiments, $R_{1'}$ is substituted phenyl moiety (e.g., a phenyl ring with 1, 2, 3, 4, or 5 substituents). In other embodiments, $R_{1'}$ is a substituted or unsubstituted heteroaryl moiety.

In certain embodiments, $R_{1'}$ is —C(O)$R_{A'}$. In other embodiments, $R_{1'}$ is —CO$_2$$R_{A'}$. In certain embodiments, $R_{A'}$ is $C_1$-$C_6$ alkyl. In certain particular embodiments, $R_{A'}$ is methyl. In certain embodiments, $R_{A'}$ is

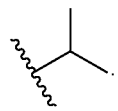

In other embodiments, $R_{A'}$ is t-butyl. In certain particular embodiments, $R_{1'}$ is —CO$_2$$R_{A'}$, wherein $R_{A'}$ is one of the formulae:

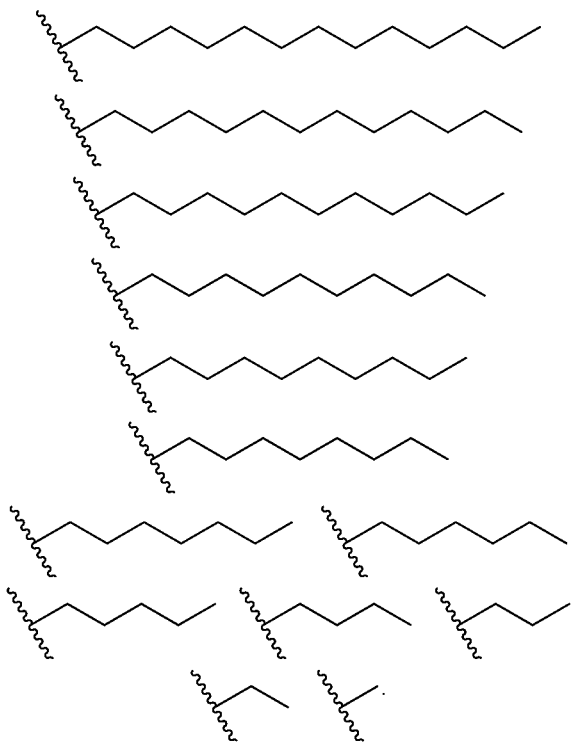

As would be appreciated by one of skill in this art, any of the above alkyl groups may be substituted, branched, unsaturated, and/or cyclic.

In certain particular embodiments, $R_{1'}$ is —CO$_2$$R_{A'}$, wherein $R_{A'}$ is:

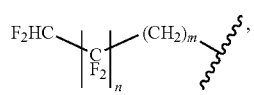

wherein n is an integer between 0 and 20, inclusive; and m is an even or odd integer between 1 and 6, inclusive.

In certain particular embodiments, $R_{1'}$ is —CO$_2$$R_{A'}$, wherein $R_{A'}$ is of the formula:

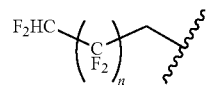

wherein n is an integer between 0 and 20, inclusive. In certain embodiments, n is an integer between 0 and 12, inclusive. In certain embodiments, n is an integer between 0 and 6, inclusive. In certain embodiments, n is an integer between 1 and 6, inclusive.

In certain particular embodiments, $R_{1'}$ is —CO$_2$$R_{A'}$, wherein $R_{A'}$ is aryl or arylalkyl. In certain particular embodiments, $R_{1'}$ is —CO$_2$$R_{A'}$, wherein $R_{A'}$ is of the formula:

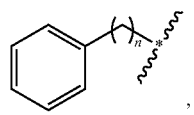

wherein n is an integer between 0 and 12, inclusive. In certain embodiments, n is 0. In certain embodiments, n is 1. In other embodiments, n is 2, 3, 4, 5, or 6. In certain particular embodiments, $R_{1'}$ is —CO$_2$$R_{A'}$, wherein $R_{A'}$ is of the formula:

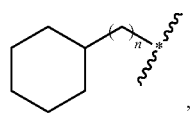

wherein n is an integer between 0 and 12, inclusive. In certain embodiments, n is 0. In certain embodiments, n is 1. In other embodiments, n is 2, 3, 4, 5, or 6.

In certain embodiments, $R_{1'}$ or $R_{2'}$ contains at least one halogen, provided that when $R_{1'}$ is halogen, $R_{2'}$ is not halogen. In certain embodiments, $R_{1'}$ or $R_{2'}$ contains at least one fluorine, provided that when $R_{1'}$ is fluorine, $R_{2'}$ is not fluorine.

In certain embodiments, $R_{2'}$ is substituted or unsubstituted, branched or unbranched aliphatic. In yet other embodiments, $R_{2'}$ is $C_1$-$C_6$ alkyl. In certain embodiments, $R_{2'}$ is an alkyl moiety. In certain particular embodiments, $R_{2'}$ is methyl. In certain particular embodiments, $R_{2'}$ is ethyl. In certain embodiments, $R_{2'}$ is propyl. In certain embodiments, $R_{2'}$ is butyl. In certain embodiments, $R_{2'}$ is a aryl or heteroaryl moiety. In certain embodiments, $R_{2'}$ is a phenyl moiety.

In certain embodiments, $R_{2'}$ is —CO$_2$$R_{A'}$, wherein $R_{A'}$ is cyclic or acyclic, branched or unbranched aliphatic substituted with one or more halogen.

In certain other embodiments, $R_{2'}$ is —CO$_2$$R_{A'}$, wherein $R_{A'}$ is:

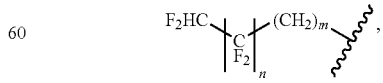

wherein n is an integer between 0 and 20, inclusive; and m is an even or odd integer between 1 and 6, inclusive.

In certain other embodiments, $R_{2'}$ is —CO$_2$$R_{A'}$, wherein $R_{A'}$ is:

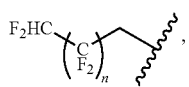

wherein n is an integer between 0 and 20, inclusive.

In certain embodiments, $R_{1'}$ is —$CO_2R_{A'}$. In other embodiments, $R_{1'}$ is —$CO_2R_{A'}$, and $R_{2'}$ is $C_1$-$C_6$ alkyl. In other embodiments, $R_{1'}$ is —$CO_2R_{A'}$, and $R_{2'}$ is methyl. In other embodiments, $R_{1'}$ is —$CO_2R_{A'}$, and $R_{2'}$ is fluorine.

In certain embodiments, $R_{1'}$ is selected from the group consisting of hydrogen, halogen and cyclic or acyclic, branched or unbranched aliphatic or aryl having up to six carbons, wherein said alkyl or aryl may optionally be substituted with one or more functional group selected from the group consisting of halogen, —OH and —$OCH_3$; and $R_{2'}$ is selected from the group consisting of $R_{A'}$, —$C(O)R_{A'}$, and —$CO_2R_{A'}$, wherein $R_{A'}$ is a cyclic or acyclic, substituted or unsubstituted, branched or unbranched aliphatic.

In certain embodiments, $R_{1'}$ is selected from the group consisting of hydrogen, halogen and cyclic or acyclic, branched or unbranched aliphatic or aryl having up to six carbons, wherein said alkyl or aryl may optionally be substituted with one or more functional group selected from the group consisting of halogen, —OH and —$OCH_3$; and $R_{2'}$ is —$CO_2H$.

In certain embodiments, the compound is a methacrylate of formula:

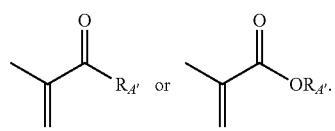

wherein $R_{A'}$ is defined to contain the methylene group of Formula (I).

In certain embodiments, the compound is a 2-fluoroacrylate of formula:

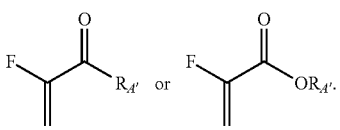

In certain embodiments, the compound is a crotonate of formula:

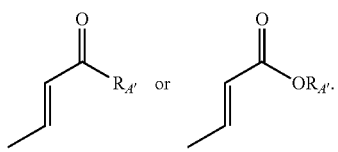

In certain embodiments, the methacrylate useful in the treatment of hair is of the formula:

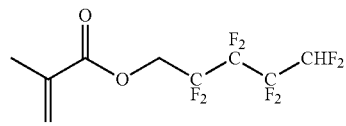 [SMILES: C=C(C)C(=O)OCC(F)(F)C(F)(F)C(F)(F)C(F)F]

In certain embodiments, a fluorinated organic compound is applied to hair based on the inventive hair treatment system. The fluorinated compound typically comprises an unsaturated functional group and at least one fluorine atom. The unsaturated functional group includes a double bond or triple bond. Exemplary unsaturated functional groups include alkenes, alkynes, carbonyls, imines, thiocarbonyls, acrylates, methacrylates, acrylates, crotonates, styrenes, nitriles, cyano, vinyl, styrene, crotonate, cinnamate, dienes, trienes, eneynes, maleimides, etc.

The fluorinated compound may range from including one fluorine atom to being one fluorine atom less than being perfluorinated. In certain embodiments, a functional group of the compound is fluorinated such as, for example, an alkyl, alkenyl, alkynyl, acyl, aryl, heteroaryl, heterocyclic, or carbocyclic moiety. In certain embodiments, the fluorinated compound includes at least 1, 2, 3, 4, 5, 6, 7, 8, 9, 10, 11, 12, 13, 14, 15, 16, 17, 18, 19, or 20 fluorine atoms. In other embodiments, the fluorinated compound contains at least 10, at least 15, at least 20, at least 25, at least 30, or at least 40 fluorine atoms. As would be appreciated by one of skill in this art, the larger the compound the more fluorine atoms the compound is likely to have. Furthermore, the compound applied to hair should include enough fluorine atoms so that the compound imparts the desired characteristics when applied to hair (e.g., look, feel).

In certain embodiments, at least 10%, 20%, 30%, 40%, 50%, 60%, 70%, 80%, 90%, 95%, or 99% of the total number of hydrogen and fluorine atoms are fluorine atoms in the fluorinated compound. In certain embodiments, at least 50% of the total number of hydrogen and fluorine atoms are fluorine atoms in the fluorinated compound. In certain embodiments, at least 80% of the total number of hydrogen and fluorine atoms are fluorine atoms in the fluorinated compound. In certain embodiments, at least 90% of the total number of hydrogen and fluorine atoms are fluorine atoms in the fluorinated compound.

In certain embodiments, the fluorinated compound is a fluorinated alkene. In certain particular embodiments, the fluorinated alkene is monosubstituted. In other embodiments, the fluorinated alkene is disubstituted. Disubstituted fluorinated alkene may be either in the cis or trans configuration or a mixture thereof. In yet other embodiments, the fluorinated alkene is trisubstituted. The trisubstituted fluorinated alkene may be in either the E or Z configuration or a mixture thereof. In still other embodiments, the fluorinated alkene is tetrasubstituted. Again, various isomers are possible and are considered part of this invention. In certain embodiments, the fluorinated compound is a fluorinated alkyne.

Exemplary monosubstituted fluorinated compounds include:

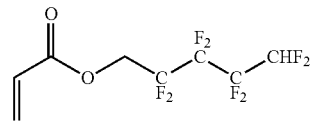

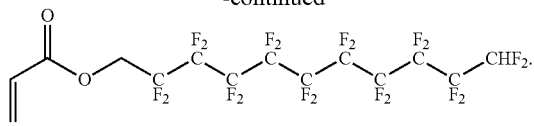

Exemplary disubstituted fluorinated compounds useful in the treatment of hair include:

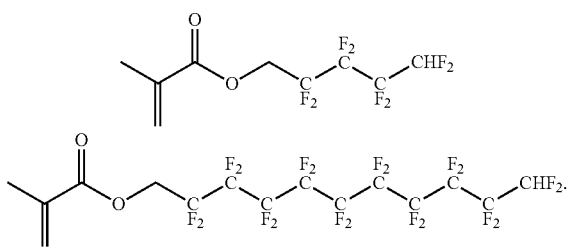

In certain embodiments, the fluorinated compound is mixed with one or more different compound. As would be appreciated by those of skill in this art, a mixture may have desirable properties not attainable with one compound alone. In certain embodiments, two different compounds are applied to hair. In other embodiments, three different compounds are applied to hair. When different compounds are used, the compounds are applied to hair simultaneously or separately. In certain embodiments, the compounds are all in the same solution which is applied to the hair. In certain embodiments, one of the compounds is fluorinated, and another is not fluorinated. In other embodiments, all compounds are fluorinated.

The compounds described herein can be applied to hair using any method known in the art. The hair to be treated is brushed, sprayed, rubbed, dipped, soaked, etc. with the compound or a solution of the compound. In certain embodiments, the compound is dissolved in a carrier such as water, alcohol, water/alcohol or alcohol/water mixtures (between 5%/95% to 10%/90%, between 10%/90% to 20%/80%, between 20%/80% to 30%/70%, between 30%/70% to 40%/60%, and between 40%/60% to 50%/50%) or other carriers and applied to hair. The carrier may include a propellant such as difluoroethane or dimethyl ether. Typically, the concentration of the compound ranges from 0.1% to 10%. In certain embodiments, the concentration ranges from 0.1% to 3%. In other embodiments, the concentration ranges from 0.1% to 2%.

The compound is typically soluble in a variety of organic carriers (e.g., alcohol), propylene glycol, glycerol, water, or aqueous solutions. In certain embodiments, the compound has a solubility of at least 10 g/dL in a 50:50 water/ethanol solution. In certain embodiments, the compound has a solubility of at least 5 g/dL in a 50:50 water/ethanol solution. In certain embodiments, the compound has a solubility of at least 4 g/dL in a 50:50 water/ethanol solution. In certain embodiments, the compound has a solubility of at least 3 g/dL in a 50:50 water/ethanol solution. In certain embodiments, the compound has a solubility of at least 2 g/dL in a 50:50 water/ethanol solution. In certain embodiments, the compound has a solubility of at least 1 g/dL in a 50:50 water/ethanol solution. In certain embodiments, the compound has a solubility of at least 0.5 g/dL in a 50:50 water/ethanol solution. An aqueous solution may be acid or basic. In certain embodiments, the compound is soluble in an alcohol (e.g., methanol, ethanol, denatured ethanol, isopropanol, butanol).

Polymerization Initiators

Preferably, the present invention does not include a polymerization initiator, more preferably it does not include a polymerization initiator that is activated under ambient or uv light or using a heat source.

Cosmetic Hair Care Compositions

The present invention provides cosmetic hair care compositions comprising an active hair care ingredient as described above, and a cosmetically acceptable excipient. Cosmetically acceptable excipients used in the hair care industry can be broken down into several categories. Components from a category may be included or excluded from the final hair care composition depending on the use of the final composition (e.g., hair spray, conditioner, shampoo). The categories of excipients include: (1) preservatives/antioxidants/chelating agents; (2) sunscreen agents; (3) vitamins; (4) dyes/hair coloring agents; (5) proteins/amino acids; (6) plant extracts; (7) humectants; (8) fragrances/perfumes; (9) oils/emollients/lubricants/butters; (10) penetrants; (11) thickeners/viscosity modifiers; (12) polymers/resins/hair fixatives/film formers; (13) surfactants/detergents/emulsifiers/opacifying agents; (14) volatiles/propellants/solvents/carriers; (15) liquid vehicles/solvents/carriers; (16) salts; (17) pH adjusting agents/buffers/neutralizing agents; (18) hair conditioning agents; (19) anti-static agents/anti-frizz agents; (20) antidandruff agents; (21) hair waving/straightening agents; and (22) absorbents.

In certain embodiments, the cosmetic hair care composition is a spray. The spray typically includes the active hair care ingredient and a carrier or propellant. In certain embodiments, the carrier is a water and alcohol mixture. In certain embodiments, the spray composition also optionally includes a preservative, antioxidant, sunscreen agent, vitamin, protein, peptide, plant extract, humectant, oil, emollient, lubricant, thickener, hair conditioning agent, polymer, or surfactant. In certain embodiments, the composition includes an oil. In certain embodiments, the composition includes a polymer. In certain embodiments, the composition includes a humectant. In certain embodiments, the composition includes a fragrance. In certain particular embodiments, the composition comprises water, an alcohol, an oil, fragrance, and an active hair care ingredient. In certain particular embodiments, the composition comprises water, an alcohol, an oil, a polymer, fragrance, and an active hair care ingredient. In certain particular embodiments, the composition comprises water, an alcohol, an anti-static agent, fragrance, and an active hair care ingredient. In certain particular embodiments, the composition comprises water, an alcohol, a hair-conditioning agent, fragrance, and an active hair care ingredient. In certain particular embodiments, the composition comprises water, an alcohol, a surfactant, fragrance, and an active hair care ingredient. In certain particular embodiments, the composition comprises water, an alcohol, an emollient, fragrance, and an active hair care ingredient. Hair spray compositions are dispensed from containers that aerosol dispensers or pump spray dispensers. Such dispensers are known in the art and are commercially available from a variety of manufacturers, including American National Can Corp. and Continental Can Corp.

In certain embodiments, when the hair spray composition is dispensed from a pressurized aerosol container, a propellant is used to force the composition out of the container. Suitable propellants are described herein. In certain embodiments, the propellant is a liquifiable gas. In certain embodiments, the propellant is a halogenated propellant. In other embodiments, the composition does not contain any fluorinated or chlorinated propellants. Generally, the amount of propellant in the composition is from about 10% to about 60% by weight. In certain embodiments, the amount of propellant in the composition ranges from about 15% to about 50% by weight. In certain embodiments, the propellant is separated from the hair spray composition as as in a two compartment container. Other suitable aerosol dispensers are those characterized by the propellant being compressed air which can be filled into the dispenser using a pump or equivalent device prior to use. Such dispensers are described in U.S. Pat. Nos. 4,077,441 and 4,850,577, both of which are incorporated by reference herein, and in U.S. patent application, U.S. Ser. No. 07/839,648, filed Feb. 21, 1992, also incorporated by reference herein. Conventional non-aerosol pump spray dispensers, i.e., atomizers, may also be used to apply the invention hair spray compositions. In certain embodiments, when the hair spray composition is dispensed from a pressurized aerosol container, the container is essentially propellant-free and uses a 'bag or bladder' in bottle to apply the invention. An example of this application is an Excel package.

In certain embodiments, the cosmetic hair care composition is a cream. The inventive cream typically includes the active hair care ingredient, a carrier, an oil, a hair conditioning agent, and a thickening agent. In certain embodiments, the cream also includes a fragrance. In certain embodiments, the cream also includes a plant extract. In certain embodiments, the cream also includes a surfactant. In certain embodiments, the cream also include a polymer. The inventive cream may be packaged in a tube, tub, bottle, or other suitable container.

According to certain embodiments, the present invention is a non-toxic hair care composition comprising a non-perfluorinated, non-polymeric compound of formula (I) described above and an excipient comprising a rheology modifier and a non-ionic emulsifier. This enables delivering a fluorinated compound in a non-alcohol aqueous sprayable gel suspension via a pseudoplastic external phase with a high zero-shear viscosity. The rheology modifier is preferably from 0.1-2.0% w/w of the composition. Examples of a rheology modifier include gyceryl polyacrylate, sodium polyacrylate, carbomer, acrylates copolymer, acrylic acid/vp crosspolymer, or xanthan gum. The non-ionic emulsifier is preferably from 0.05-5.0% w/w of the composition. Examples of a non-ionic emulsifier include Laureth-23, Octyldodeceth-20, Oleth-10, Peg-40 Hydrogenated Castor Oil, Polaxomer 127, Polysorbate 20, or Ceteareth-20. Other rheology modifiers and non-ionic emulsifiers not specifically mentioned above are commercially available and known to those of ordinary skill in the art. Other excipients, suitable for hair care products, may be added to the non-alcohol spray to achieve desired functionality.

Moisture Resistance

Moisture on hair and its penetration into the hair can disturb the arrangement of hair proteins, resulting in cosmetically undesired changes, such as, an increase of frizz. The present invention provides hair, in particular hair on or from the scalp, with beneficial moisture resistance properties. Moisture resistance in the present invention refers to the hysteresis of water sorption/desorption when measured by Dynamic Vapor Sorption (DVS). In DVS a sample is placed on a microbalance exposed to a continuous flow of air with predetermined and constant relative humidity. As the humid air passes over the sample, a zone of constant moisture concentration is created around it. This zone allows the rapid establishment of water vapor sorption or desorption equilibrium by maximizing mass transport of water vapor into and out of the sample.

Mass changes in the sample (e.g., a swatch of hair) due to water vapor sorption/desorption can be measured between different levels of relative humidity at a particular temperature. The change in mass can be plotted as a function of the relative humidity, which provides information about the nature of water vapor sorption phase (absorption and/or adsorption) when humidity is increased, or, conversely, the nature of desorption of water, when humidity is decreased. The difference in changes in mass at any particular value for relative humidity in the sorption and desorption phases is known as the hysteresis and can be used as a measure to evaluate the ability of a hair treatment to resist or control moisture on and in hair. As described below, the invention affords reduced hysteresis especially over relative humidity values range of 30-80% RH.

In the context of the present invention, moisture resistance is measured according to DVS Protocol I. A "decrease in moisture flux" means that treated hair exhibits a decrease in hysteresis when subjected to dynamic vapor sorption according to DVS Protocol I.

DVS Protocol I 1. 1.50 g of bleached hair tress (standard single bleached, wavy frizzy hair from International Hair Importers, White Plains N.Y., USA) is dampened with 0.30 mL de-ionized water, optionally via pipet, and lightly combed through to remove any tangles.
2. Apply composition to the hair tress according to the following amounts: for a serum (0.09 g to 0.12 g), for a cream/lotion/mousse (0.20 g to 0.25 g), and for a spray (0.35 g to 0.40 g) and is distributed evenly and combed through the hair. Preferably the weight ratio of formulation to hair should be approximately 0.073 for serums, 0.15 for a cream/lotion/mousse and 0.25 for a spray.
3. Styling consists of 10 passes with a hair brush and blow drier set to high, approximately 50-120° C.
4. After styling, the hair is cut and sections from the middle of each tress (approximately 300 mg) are analyzed via DVS.
5. DVS conditions are as follows. Unless otherwise stated the temperature employed is 25° C. Sorption phase: Start at 30% RH and increase up to 90% RH, each step increasing RH by 10%. Desorption phase: Start at 90% RH and decrease down to 0% RH, each step decreasing RH by 10%. At each RH condition, the sample is maintained for 4 hours, and the step up or down to the next RH level is programmed to occur over 20 min period.

Monitoring the hysteresis values from such a DVS experiment on hair samples allows assessment of the ability of a hair treatment to resist or control moisture.

The present invention affords superior moisture resistance compared to either (1) a control treatment using water and (2) a silicone product, such as Kérastase® Oleo Relax Serum (purchased in the USA, 2008; hereinafter "Commercial Example A"), which in fact increased the hysteresis compared to water. Preferably, use of the invention on a hair tress as described above affords a 4% reduction in the average hysteresis values compared to control (water-treated) hair over the relative humidity range of 30-80% when examined by the DVS protocol described above. More preferably, use of the invention on a hair tress as described above affords more than a 10% reduction and still more preferably more than a 20% reduction, in the average hysteresis values compared to control (water treated) hair over the relative humidity range of 30-80% when examined by the DVS protocol described above. Even more preferably, the invention affords a 50% or more, or even an 80% or more, reduction in the average hysteresis values compared to control (water-treated) hair over the relative humidity values range of 30-80% RH when determined by the DVS protocol described above.

Weightlessness

Those who use hair care products desire the beneficial effects described above. However, such users do not want the feeling of residue/product in or on their hair. A composition that maintains performance, but which does so with less residual weight or "feel" in the hair is, therefore, preferred.

The compositions of the present invention, while maintaining product performance, beneficially lose no less than 25% of their weight, preferably 50% of their weight, more preferably no less than 70% of their weight, still more preferably no less than 80% weight, and still more preferably no less than 90%, and most preferably 95% or higher of their weight after heating at 55° C. and 10% RH for 10 minutes (for spray formulations) and 30 minutes (cream/lotion/serum/mousse) formulations according to the "Weightlessness Test I."

Weightless Test I

Composition is dispensed into an uncovered container and spread out evenly. For instance, the container is a round container with a diameter of 9 cm and a lip measuring 0.5 cm.
1. The containers are labeled and then weighed immediately before and after dosing with 3 g of formulation.
2. Compositions are left to equilibrate at ambient conditions (25° C., 30% RH) for 5 minutes before placing into the oven.
3. The container is placed into an oven controlled at 55° C. and 10% RH.
4. Each dish is removed and its mass recorded at 10 minutes for spray compositions and 30 minutes for cream/lotion/serum/mousse compositions.

The compositions for treating hair according to the invention on average leave at least 25% less residue upon drydown when following package instructions for amounts used for Kérastase® Oleo Relax Serum ("Commercial Example A"), John Frieda® Frizz Ease ("Commercial Example B"), Biosilk® Silk Therapy ("Commercial Example H"), Redken® Smooth Down Heat Glide ("Commercial Example C"), Nexxus® Sleek Memory Straightening Smooth Spray ("Commercial Example D"), Barex® Re-define Crème ("Commercial Example G"), Fekkai® Glossing Cream ("Commercial Example E") and Bedhead® Curls Rock ("Commercial Example F") (all purchased in the USA; 2008). It is believed that one reason for the "weightlessness" benefits of the inventive formulations is that they do not require, and preferably do not include, silicone compounds at levels found in the above identified hair care products.

Dirt Resistance

Many materials are used to control or reduce moisture penetration into hair fibers. However, the majority of these materials are oil-based or silicone-based. The resulting effect is modest moisture resistance combined with a heavy residue feel which attracts grease and particulates. It is desirable in the art to create a composition that will control or reduce moisture penetration into hair fibers while leaving the hair feeling lightweight, non-greasy, and minimizing attraction of dirt/particulates.

The attraction of dirt and particles to the hair leaves the hair limper, heavier, and duller throughout the day. The ability to resist environmental pollutants gives the hair longer lasting style and shine. Accordingly, the ability of the present inventive hair care compositions to resist dirt accumulation was examined and compared to Commercial Example A. Corn starch was selected as simulated dirt. USP corn starch is uniformly-white and can associate with hair, providing excellent contrast on black hair, thereby allowing for a quantifiable Gray-scale measurement via digital photography. Remaining corn starch was also assayed by gravimetric analysis.

Starch Resistance (Gravimetric)

The inventive hair care compositions when tested on hair as described below should afford gain in weight of no more than 15% by weight, preferably no more than 10% by weight, more preferably no more than 7% weight, and most preferably no more than 5% by weight when subjected to Starch Test I. As a measure of resisting dirt, "weight gain" refers to the weight gain measured according to Starch Test I.

Starch Test I 1. 1.50 g of virgin dark brown hair tress (International Hair Importers, White Plains N.Y., USA) is dampened with 0.30 mL of water, optionally via pipette.
2. Apply composition to the hair tress according to the following amounts: for a serum (0.10 g to 0.12 g), for a cream/lotion/mousse (0.20 g to 0.25 g), and for a spray (0.35 g to 0.40 g) and is distributed evenly and combed through the hair. Preferably the weight ratio of formulation to hair should be approximately 0.073 for serums, 0.15 for a cream/lotion/mousse and 0.25 for a spray.
3. The hair was styled with a hair brush and blow drier on high speed and high temperature, approximately at 50-120° C. for 30 seconds.
4. The tress is saturated in a bath of corn starch, for instance, in about 2 grams of corn starch, USP.
5. The tress is removed from the corn starch bath and shaken by hand until all loose corn starch is removed, for instance, for 10 seconds.
6. The tress is weighed and the new mass is recorded.

The present invention may be used on any animal with hair. The system is particularly useful for treating human hair. However, the hair or fur of other mammals may also be treated. For example, the hair or fur of domesticated animals such as dogs and cats may be treated using the inventive system. In addition, the hair or fur of test animals such as rodents (e.g., mouse, rat, rabbit, guinea pig, etc.) or primates may also be treated. In certain embodiments, hair samples from a human (e.g., hair clippings) or other animals are tested with the present invention. Hair or fur samples treated with the present invention are considered to be within the scope of the invention. These hair or fur samples comprise compound on the hair or fur. In certain embodiments, the hair is human hair. In other embodiments, the hair is non-human hair. In certain embodiments, the hair or fur is dog or cat hair or fur. In other embodiments, the hair is rat, mouse, guinea pig, rabbit, gerbil, or primate hair. The hair treatment system of the present invention can also be used to treat hair contained in wigs, toupees, and hairpieces.

These and other aspects of the present invention will be further appreciated upon consideration of the following Examples, which are intended to illustrate certain particular embodiments of the invention but are not intended to limit its scope, as defined by the claims.

EXAMPLES

Example 1—Testing of Treated Hair

Tests as described herein may be used to test shine/luster, break strength, and hair fiber thickness.

In this example, the measure of the hair's shine/luster is proposed. After applying a composition and curling and brushing a hair sample, the hair would be wound around a cylinder and placed under a lamp that mimics sunlight. The width of the cone of luster will be measure and compared with that of a commercial product.

In this example, the measure of the hair's break strength is proposed. Single hair fibers (treated and untreated) can be attached to an Instron which will pull at one end of the fiber, breaking the fiber at a certain force.

In this example, the measure of the hair fiber thickness is proposed. Cross sections of hair fibers (treated and untreated) can be examined and measured by microscopy.

In this example, the humidity resistance of the treated hair is proposed. This property can be measured by placing the styled hair tress in an atmosphere of high humidity.

In this example, the feel is proposed. The parameters of feel can be assessed for a given material on the hair fiber. Several parameters such as tack, slip, stiffness, smoothness, grease, and strength can be evaluated by a blind test of experts.

Example 2—Styling Spray

Below are included various hair care compositions of the exemplary fluorinated compounds. The fluorinated compounds may be, for example, 2,2,3,3,4,4,5,5-octafluoro-1,6-hexyl dimethacrylate; 2,2,3,3,4,4,5,5-octafluoro-1,6-hexyl diacrylate; 2,2,3,3,4,4,5,5-octafluoro-1,6-hexyldiacrylate; 2,2,3,3,4,4,5,5-octafluoro-1,6-hexyldimethacrylate; 2,2,3,3,4,4,5,5-octafluoropentyl methacrylate; 2,2,3,3,4,4,5,5-octafluoropentyl acrylate; 2,2,3,3,4,4-hexafluoro-1,5-pentyl diacrylate; 2,2,3,3,4,4-hexafluoro-1,5-pentyl dimethacrylate; or any of the other fluorinated compounds used in the present invention as described above. As would be appreciated by one of skill in the art, these formulations may be used to deliver other compounds described herein such as other methacrylates, acrylates, alkenes, halogenated compounds, etc. An exemplary styling spray containing a fluorinated compound may include:

| | |
|---|---|
| Water | 45-51% w/w |
| Alcohol (e.g., ethanol) | 40-55% w/w |
| PEG-40 Hydrogenated Castor Oil | 0.1-5% w/w |
| Fragrance | 0.1-1.5% w/w |
| Fluorinated compound | 0.1-10% w/w |

Example 3—Styling Spray

An exemplary styling spray containing a fluorinated compound may include:

| | |
|---|---|
| Water | 45-51% w/w |
| Alcohol (e.g., ethanol) | 40-55% w/w |
| VP/Vinyl Caprolactam/DMAPA Acrylates Copolymer | 0.01-2% w/w |
| PEG-40 Hydrogenated Castor Oil | 0.01-5% w/w |
| Fragrance | 0.1-1.5% w/w |
| Fluorinated compound | 0.1-10% w/w |

The fluorinated compound is as described in Example 2 above.

Example 4—Styling Spray

Another exemplary styling spray may include:

| | |
|---|---|
| Water | 45-51% w/w |
| Alcohol (e.g., ethanol) | 40-55% w/w |
| PVP/VA | 0.01-2.5% w/w |
| PEG-40 Hydrogenated Castor Oil | 0.1-5% w/w |
| Fragrance | 0.1-1.5% w/w |
| Fluorinated compound | 0.1-10% w/w |

The fluorinated compound is as described in Example 2 above.

Example 5—Styling Spray

An exemplary styling spray containing a fluorinated compound may include:

| | |
|---|---|
| Water | 45-51% w/w |
| Alcohol (e.g., ethanol) | 40-55% w/w |
| Cetrimonium chloride | 0.01-2.5% w/w |
| PPG-2 myristyl ether propionate | 0.01-2.5% w/w |
| PEG-40 hydrogenated castor oil | 0.01-5% w/w |
| Fragrance | 0.1-1.5% w/w |
| Fluorinated compound | 0.1-10% w/w |

The fluorinated compound is as described in Example 2 above.

Example 6—Styling Spray

Another exemplary styling spray containing a fluorinated compound may include:

| | |
|---|---|
| Water | 45.0-51.0% w/w |
| Alcohol (e.g., ethanol) | 40.0-55.0% w/w |
| Glycereth-7 | 0.1-2.5% w/w |
| PEG-40 Hydrogenated Castor Oil | 0.1-5.0% w/w |
| Fragrance | 0.1-1.5% w/w |
| Fluorinated compound | 0.1-10% w/w. |

The fluorinated compound is as described in Example 2 above.

Example 7—Styling Cream

An exemplary styling cream containing a fluorinated compound may include:

| | |
|---|---|
| Water | 75-97% w/w |
| Polysorbate 80 | 0.1-2.0% w/w |
| Isohexadecane | 0.1-2.0% w/w |
| Acrylamide/Sodium Acryloyldimethyltaurate copolymer | 0.1-1.0% w/w |
| PPG-2 Myristyl Ether Propionate | 0.1-3% w/w |

-continued

| | |
|---|---|
| Phenoxyethanol | 0.1-1.0% w/w |
| Methylparaben | 0.1-0.5% w/w |
| Propylparaben | 0.1-0.5% w/w |
| Fragrance | 0.1-1.5% w/w |
| Fluorinated compound | 0.1-10% w/w |

The fluorinated compound is as described in Example 2 above.

Example 8—Styling Cream

An exemplary styling cream containing a fluorinated compound may include:

| | |
|---|---|
| Water | 75-97% w/w |
| Polysorbate 20 | 0.1-1.0% w/w |
| Polyacrylate-13 | 0.5-3.5% w/w |
| Polyisobutene | 0.5-3.5% w/w |
| Ethylhexyl Stearate | 0.1-3% w/w |
| Phenoxyethanol | 0.3-1.5% w/w |
| Caprylyl glycol | 0.1-1.0% w/w |
| Sorbic acid | 0.1-0.5% w/w |
| Cetyl Alcohol | 0.25-1.5% w/w |
| Fragrance | 0.1-1.5% w/w |
| Fluorinated compound | 0.1-10% w/w |

The fluorinated compound is as described in Example 2 above.

Example 9—Styling Cream

An exemplary styling cream containing a fluorinated compound may include:

| | |
|---|---|
| Water | 75-97% w/w |
| Cetearyl Alcohol | 1.5-5% w/w |
| Glyceryl Stearate | 0.5-3% w/w |
| Ceteareth-20 | 0.5-3% w/w |
| PPG-2 Myristyl Ether Propionate | 0.1-3% w/w |
| Phenoxyethanol | 0.1-1.5% w/w |
| Fragrance | 0.1-1.5% w/w |
| Fluorinated compound | 0.1-10% w/w |

The fluorinated compound is as described in Example 2 above.

Example 10—Styling Spray

An exemplary styling spray containing a fluorinated compound may include:

| | |
|---|---|
| Water | 45-94% w/w |
| Alcohol (e.g., ethanol) | 5-45% w/w |
| Stearyl alcohol | 0.5-3% w/w |
| Laureth-23 | 0.1-2% w/w |
| Laureth-4 | 0.1-2% w/w |
| PEG-40 Hydrogenated Castor Oil | 0.1-2% w/w |
| Fragrance | 0.1-1.5% w/w |
| Fluorinated compound | 0.1-10% w/w |

The fluorinated compound is as described in Example 2 above.

Example 11—Styling Cream

An exemplary styling cream containing a fluorinated compound may include:

| | |
|---|---|
| Water | 72-97% w/w |
| Behenyl alcohol | 1.5-5% w/w |
| Ceteareth-20 | 0.5-5% w/w |
| Ceteth-10 | 0.5-5% w/w |
| PEG-40 Stearate | 0.25-1% w/w |
| Hydroxypropyltrimonium Hydrolyzed Corn Starch | 0.25-1.5% w/w |
| PPG-3 Benzyl Ether Myristate | 0.1-1% w/w |
| Carbomer | 0.01-0.5% w/w |
| Triethanolamine | 0.01-0.8% w/w |
| Fragrance | 0.1-1.5% w/w |
| Fluorinated compound | 0.1-10% w/w |

The fluorinated compound is as described in Example 2 above.

Example 12—Styling Cream

An exemplary styling cream containing a fluorinated compound may include:

| | |
|---|---|
| Water | 75-97% w/w |
| Cetearyl alcohol | 1.5-5% w/w |
| Ceteareth-20 | 0.5-5% w/w |
| Ceteth-10 | 0.5-5% w/w |
| Behentrimonium Chloride | 0.1-2.5% w/w |
| PPG-2 Myristyl Propionate | 0.25-3% w/w |
| Carbomer | 0.01-.5% w/w |
| Triethanolamine | 0.01-0.8% w/w |
| Fragrance | 0.1-1.5% w/w |
| Fluorinated compound | 0.1-10% w/w |

The fluorinated compound is as described in Example 2 above.

Example 13—Styling Cream

Another formulation of styling cream containing a fluorinated compound may include:

| | |
|---|---|
| Water | 75-97% w/w |
| Cetearyl alcohol | 1.5-5.0% w/w |
| Ceteareth-20 | 0.5-5.0% w/w |
| Ceteth-10 | 0.5-5.0% w/w |
| VP/Acrylates/Lauryl Methacrylate Copolymer | 0.01-2.5% w/w |
| PPG-2 Myristyl Propionate | 0.25-3.0% w/w |
| Carbomer | 0.01-0.5% w/w |
| Triethanolamine | 0.01-0.9% w/w |
| Fragrance | 0.1-1.5% w/w |
| Fluorinated compound | 0.1-10% w/w |

The fluorinated compound is as described in Example 2 above.

Example 14—Styling Cream

Another exemplary formulation of styling cream containing a fluorinated compound may include:

| | |
|---|---|
| Water | 75-97% w/w |
| Cetearyl alcohol | 1.5-5% w/w |
| Ceteareth-20 | 0.5-5% w/w |
| Ceteth-10 | 0.5-5% w/w |
| Polyquaternium-28 | 0.5-10% w/w |
| PPG-2 Myristyl Propionate | 0.25-3% w/w |
| Sodium Polyactylate | 0.01-0.5% w/w |
| Preservative | 0.00-2% w/w |
| Fragrance | 0.1-1.5% w/w |
| Fluorinated compound | 0.1-10% w/w |

The fluorinated compound is as described in Example 2 above.

Example 15—Styling Cream

Another exemplary formulation of styling cream containing a fluorinated compound may include:

| Ingredients | % w/w |
| --- | --- |
| Water | 75.00-97.00 |
| Cetearyl Alcohol | 2.00-5.00 |
| Polysorbate 80 | 1.00-4.00 |
| PEG-4M | 0.25-2.00 |
| Preservative | 0.00-2.00 |
| Fragrance | 0.10-1.50 |
| Fluorinated compound | 0.10-10.00 |

The fluorinated compound is as described in Example 2 above.

Example 16—Styling Cream

An exemplary styling cream containing a fluorinated compound may include:

| Ingredients | % w/w |
| --- | --- |
| Water | 75.00-97.00 |
| Cetearyl Alcohol | 1.50-5.00 |
| Steareth-21 | 0.50-5.00 |
| Steareth-20 | 0.50-5.00 |
| VP/Acrylates/Lauryl Methacrylate Copolymer | 0.01-2.50 |
| PPG-2 Myristyl Propionate | 0.25-3.00 |
| Carbomer | 0.01-0.50 |
| Triethanolamine | 0.01-0.80 |
| Preservative | 0.00-2.00 |
| Fragrance | 0.10-1.50 |
| Fluorinated compound | 0.10-10.00 |

The fluorinated compound is as described in Example 2 above.

Example 17—Styling Spray

An exemplary styling spray containing a fluorinated compound may include:

| Ingredients | % w/w |
| --- | --- |
| Water | q.s. |
| Alcohol (e.g. ethanol) | 0.00-55.00 |
| VP/Vinyl Caprolactam/DMAPA Acrylates Copolymer | 0.00-15.00 |
| VP/Acrylates/Lauryl Methacrylate Copolymer | 0.00-15.00 |
| C10-40 Isoalkylamidopropyl Ethyldimonium Ethosulfate | 0.00-2.00 |
| Cosmetic Fluid CF-76 or CF-61 | 0.00-99.00 |
| Cetrimonium chloride | 0.00-0.50 |
| Oleic Acid | 0.00-2.00 |
| Stearyl Alcohol | 0.00-3.00 |
| Glycereth-7 | 0.00-4.00 |
| Laureth-23 | 0.00-6.00 |
| Laureth-4 | 0.00-6.00 |
| Polysorbate 80 | 0.00-6.00 |
| Sorbitan Oleate | 0.00-4.00 |
| PEG-40 Hydrogenated Castor Oil | 0.00-6.00 |
| Fragrance | 0.00-4.00 |
| Fluorinated compound | 0.10-20.00 |

The fluorinated compound is as described in Example 2 above.

Example 18—Non-Alcohol Aqueous Styling Spray Gel

The fluorinated compound was first preblended with a non-ionic emulsifier. Preblending of the emulsifier and fluorinated compound ensures proper formation of the suspended emulsion droplets resulting in a single or multi bi-layer coating of the fluorinated compound. The concentration of emulsifier remained under the CMC (critical micelle concentration) as micelle formation does not improve the stability of the suspension. The composition was homogenized such that the droplet size was less than 15 microns. This allows for lower oil to emulsifier ratio, proper dispersion of the suspended droplets and stability of the composition. The result was an aqueous based suspension of coated fluorinated compound, which resists coalescence, flocculation, and/or phase separation of the fluorinated compound. Applying shear to the compositor (e.g. spray pump), reduces the viscosity and allows for delivery of the fluorinated compound via a uniform spray pattern. Removal of the shear, allows the viscosity to recover and the composition to stabilize.

A general exemplary composition of a non-alcohol aqueous styling spray gel containing a fluorinated compound may include:

| Ingredients | % w/w |
| --- | --- |
| Water | q.s. |
| Rheology modifier | 0.10-8.00 |
| Non-ionic emulsifier | 0.05-5.00 |
| Preservative | 0.00-2.00 |
| Fragrance | 0.00-4.00 |
| Fluorinated compound | 0.10-10.00 |

The fluorinated compound is as described in Example 2 above.

Example 19—Non-Alcohol Aqueous Styling Spray Gel

A more specific exemplary of a non-alcohol aqueous styling spray gel containing a fluorinated compound may include:

| Ingredients | % w/w |
| --- | --- |
| Water | q.s. |
| Glyceryl Polyacrylate and Glycerin (Lubrajel II XD) | 0.50-7.00 |
| Octyldodeceth-20 | 0.05-5.00 |
| Phenoxyethanol (and) Methylisothiazolinone | 0.00-2.00 |
| Fragrance | 0.00-4.00 |
| Fluorinated compound | 0.10-10.00 |

The fluorinated compound is as described in Example 2 above.

The above composition may be manufactured using the process described below.

Phase A consisting of water and Lubrajel II XD: First, a vessel was charged with water and heated to 35° C. Then, 10% of the total amount of Lubrajel II XD was added and mixed for at least 20 minutes. Phase B consisting of a mixture of fluorinated compound, octyldodeceth-20, and fragrance: In a separate vessel, octyldodeceth-20 was warmed to 35° C. The fluorinated compound and fragrance were then added to the vessel. The contents were mixed until homogeneous. Phase B was added to Phase A and they were mixed until homogeneous. The mixture was then homogenized to reduce the particle size to 5-15 microns, then mixed slowly with a pitched blade propeller and allowed to de-aerate. Phase C consisting of the remaining Lubrajel II XD and a preservative: Components of Phase C were then added to the above mixture of Phase A and Phase B and mixed for 1 hour. The mixture was then cooled to 21° C.-25° C.

Example 20—Non-Alcohol Aqueous Styling Spray Gel

To further stabilize a non-alcohol aqueous styling spray gel containing a fluorinated compound with a specific gravity greater than 1.00, a low specific gravity material, such as a paraffin blend, may be added to the composition. The addition of the lower specific gravity material balances the oil phase specific gravity to 1.00, allowing for greater suspension stability.

A general exemplary composition of a non-alcohol aqueous styling spray gel containing a fluorinated compound may include:

| Ingredients | % w/w |
| --- | --- |
| Water | q.s. |
| Rheology modifier | 0.10-8.00 |
| Non-ionic emulsifier | 0.05-5.00 |
| Paraffin blend | 0.10-12.00 |
| Preservative | 0.00-2.00 |
| Fragrance | 0.00-4.00 |
| Fluorinated compound | 0.10-10.00 |

The fluorinated compound is as described in Example 2 above.

Example 21—Non-Alcohol Aqueous Styling Spray Gel

A more specific exemplary of a non-alcohol aqueous styling spray gel containing a fluorinated compound may include:

| Ingredients | % w/w |
| --- | --- |
| Water | q.s. |
| Acrylic Acid/VP Crosspolymer | 0.20-1.00 |
| Aminomethyl Propanol | 0.05-0.75 |
| SiClone SR-5 (Presperse LLC) | 0.10-12.00 |
| Laureth-23 | 0.05-5.00 |
| Laureth-4 | 0.05-5.00 |
| Phenoxyethanol (and) Methylisothiazolinone | 0.00-2.00 |
| Fragrance | 0.00-4.00 |
| Fluorinated compound | 0.10-10.00 |

The fluorinated compound is as described in Example 2 above.

The above composition may be manufactured using the process described below.

Phase A consisted of water, aminomethyl propanol (AMP) and acrylic acid/VP crosspolymer. A vessel was charged with water and heated to 50° C. Then, 10% of the total amount of AMP needed was added. Acrylic acid/VP copolymer was then added with high agitation and mixed for at least 1 hour. Phase B consisted of a mixture of fluorinated compound, Laureth-23, Laureth-4, and SiClone SR-5. In a separate vessel, fluorinated compound, Laureth-23, Laureth-4, and SiClone SR-5 were prelended at 37° C. Phase B was added to Phase A and mixed until homogeneous. The mixture was then cooled to 30° C. and homogenized to reduce the particle size to 5-15 microns. The mixture was then mixed slowly with a pitched blade propeller and allowed to de-aerate. Phase C consisted of the remaining AMP. Phase C was then added to the above mixture of Phase A and Phase B and mixed for 1 hour. The mixture was then cooled to 21° C.-25° C.

Example 22—Styling Cream

An exemplary styling cream containing a fluorinated compound may include:

| Ingredients | % w/w |
| --- | --- |
| Water | q.s. |
| Myristyl Alcohol | 0.00-5.00 |
| Cetyl Alcohol | 0.00-5.00 |
| Cetearyl Alcohol | 0.00-5.00 |
| Behenyl alcohol | 0.00-5.00 |
| Glyceryl Stearate | 0.00-2.00 |
| VP/VA Copolymer | 0.00-15.00 |
| VP/Dimethylaminoethyl Methacrylate Copolymer | 0.00-15.00 |
| VP/Acrylates/Lauryl Methacrylate Copolymer | 0.00-15.00 |
| Ceteareth-20 | 0.00-6.00 |
| Ceteth-10 | 0.00-6.00 |
| PEG-100 Stearate | 0.00-3.50 |
| PEG-40 Stearate | 0.00-3.50 |
| Polyacrylate-13 | 0.00-4.00 |
| Acrylamide/Sodium Acryloyldimethyltaurate Copolymer | 0.00-4.00 |
| Isohexadecane | 0.00-5.00 |
| Polyisobutene | 0.00-5.00 |
| Polysorbate 80 | 0.00-6.00 |
| Polysorbate 20 | 0.00-6.00 |
| Sorbitan Oleate | 0.00-4.00 |
| Ethylhexyl Stearate | 0.00-10.00 |
| PPG-2 Myristyl Propionate | 0.00-10.00 |
| PPG-3 Benzyl Ether Myristate | 0.00-10.00 |
| Hydroxypropyltrimonium Hydrolyzed Corn Starch | 0.00-5.00 |
| Carbomer | 0.00-1.00 |
| Triethanolamine | 0.00-0.75 |
| Preservative | 0.00-2.00 |
| Fragrance | 0.00-4.00 |
| Fluorinated compound | 0.10-20.00 |

The fluorinated compound is as described in Example 2 above.

Example 23—Styling Pomade

An exemplary styling pomade containing a fluorinated compound may include:

| Ingredients | % w/w |
| --- | --- |
| Water | q.s. |
| Behenyl Alcohol | 0.00-10.00 |
| Cetearyl Alcohol | 0.00-10.00 |
| Linoleum Acid | 0.00-10.00 |
| Oleth-20 | 0.00-6.00 |
| Oleth-2 | 0.00-6.00 |
| PEG-8 Beeswax | 0.00-3.50 |
| Capric/Caprylic Triglyceride | 0.00-5.00 |
| Polyquaternium -46 | 0.00-10.00 |
| PVP | 0.00-10.00 |
| Preservative | 0.00-2.00 |
| Fragrance | 0.00-4.00 |
| Fluorinated compound | 0.10-20.00 |

The fluorinated compound is as described in Example 2 above.

Example 24—Aerosol Hair Styling Spray

An exemplary aerosol hair styling spray containing a fluorinated compound may include:

| Ingredients | % w/w |
|---|---|
| Water | q.s. |
| Propellant | 2.00-80.00 |
| Alcohol (e.g. ethanol) | 0.00-55.00 |
| Polysorbate 20 | 0.00-6.00 |
| PEG-40 Hydrogenated Castor Oil | 0.00-6.00 |
| Oleth-20 | 0.00-6.00 |
| VP/VA Copolymer | 0.00-15.00 |
| Fragrance | 0.00-4.00 |
| Preservative | 0.00-2.00 |
| Fluorinated compound | 0.10-20.00 |

The fluorinated compound is as described in Example 2 above.

Example 25—Aerosol Hair Styling Mousse

An exemplary aerosol hair styling mousse containing a fluorinated compound may include:

| Ingredients | % w/w |
|---|---|
| Water | q.s. |
| Propellant | 1.00-10.00 |
| Cocamidopropylbetaine | 0.00-5.00 |
| Lauramide Oxide | 0.00-2.00 |
| Trideceth-12 | 0.00-5.00 |
| PEG-8 Stearate | 0.00-0.50 |
| Fluorinated compound | 0.10-20.00 |

The fluorinated compound is as described in Example 2 above.

Example 26—Aerosol Shave Cream

An exemplary aerosol shave cream containing a fluorinated compound may include:

| Ingredients | % w/w |
|---|---|
| Water | q.s. |
| Fatty Acid | 2.00-15.00 |
| Triethanolamine | 1.00-15.00 |
| Propellant | 2.00-6.00 |
| Laureth-23 | 0.00-2.00 |
| Hydroxyethylcellulose | 0.00-1.00 |
| Xanthan Gum | 0.00-1.00 |
| PEG-150 Distearate | 0.00-0.75 |
| Fragrance | 0.00-2.00 |
| Preservative | 0.00-1.50 |
| Fluorinated compound | 0.10-20.00 |

The fluorinated compound is as described in Example 2 above.

Example 27—Aerosol Shave Gel

An exemplary aerosol shave gel containing a fluorinated compound may include:

| Ingredients | % w/w |
|---|---|
| Water | q.s. |
| Fatty Acid | 0.00-10.00 |
| Sarcosinate Acid | 0.00-10.00 |
| Triethanolamine | 0.00-10.00 |
| Propellant | 2.00-5.00 |
| Glyceryl Oleate | 0.00-4.00 |
| Hydroxyethylcellulose | 0.00-1.50 |
| PEG-90M | 0.00-0.75 |
| Fragrance | 0.00-2.00 |
| Preservative | 0.00-1.50 |
| Fluorinated compound | 0.10-20.00 |

The fluorinated compound is as described in Example 2 above.

Example 28—Shave Cream

An exemplary shave cream containing a fluorinated compound may include:

| Ingredients | % w/w |
|---|---|
| Water | q.s. |
| Fatty Acid | 2.00-15.00 |
| Potassium Hydroxide | 0.50-10.00 |
| Sodium Lauryl Sarcosinate | 0.00-5.00 |
| Hydroxyethylcellulose | 0.00-2.00 |
| Hydroxypropylcellulose | 0.00-2.00 |
| Oleth-20 | 0.00-4.00 |
| Laureth-23 | 0.00-4.00 |
| PEG-24M | 0.00-1.00 |
| Fragrance | 0.00-2.00 |
| Preservative | 0.00-1.50 |
| Fluorinated compound | 0.10-20.00 |

The fluorinated compound is as described in Example 2 above.

Example 29—Hair Spray A

An exemplary styling spray containing a fluorinated compound may include:

| | |
|---|---|
| Denatured Alcohol | 55.0% w/w |
| Water | 38.92% w/w |
| Fluorinated compound | 2% w/w |
| PEG-40 Hydrogenated Castor Oil | 0.15% w/w |
| Fragrance | 0.50% w/w |
| $C_{10-40}$ Isoalkylamidopropyl ethyldimonium Ethosulfate | 0.25% w/w |
| Dipropylene Glycol | 0.38% w/w |

The fluorinated compound is as described in Example 2 above.

The above composition may be manufactured using the process described below.

Phase A consisting of denatured alcohol and water: First, a vessel is charged with water. Then, denatured alcohol is added to the charged vessel. The contents are mixed until homogeneous Phase A is obtained. Phase B consisting of a mixture of the fluorinated compound, PEG-40 hydrogenated castor oil and fragrance: In a separate vessel, PEG-40 hydrogenated castor oil is warmed to 30° C. The fluorinated compound and fragrance are then added to the vessel. The contents are mixed until homogeneous Phase B is obtained. Phase B is added to Phase A and they are mixed until homogeneous. Phase C consisting of $C_{10-40}$ isoalkylamidopropyl ethyldimonium ethosulfate and dipropylene glycol: Phase C is added to the above mixture of Phase A and Phase B until a homogeneous composition above is obtained.

Example 30—Hair Spray B

An exemplary styling spray containing a fluorinated compound may include:

| | |
|---|---|
| Denatured Alcohol | 55.50% w/w |
| Water | 37.47% w/w |
| VP/Vinyl Caprolactam/DMAPA Acrylates Copolymer | 3.75% w/w |
| Fluorinated compound | 2.00% w/w |
| PEG-40 Hydrogenated Castor Oil | 0.15% w/w |
| Fragrance | 0.50% w/w |
| $C_{10-40}$ Isoalkylamidopropyl ethyldimonium Ethosulfate | 0.25% w/w |
| Dipropylene Glycol | 0.38% w/w |

The fluorinated compound is as described in Example 2 above.

The above composition may be manufactured using the process described below.

Phase A consisting of denatured alcohol and water: First, a vessel is charged with water. Then, denatured alcohol is added to the charged vessel. The contents are mixed until homogeneous Phase A is obtained. Phase B consisting of a mixture of the fluorinated compound, PEG-40 hydrogenated castor oil and fragrance: In a separate vessel, PEG-40 hydrogenated castor oil is warmed to 30° C. The fluorinated compound and fragrance are then added to the vessel. The contents are mixed until homogeneous Phase B is obtained. Phase B is added to Phase A and they are mixed until homogeneous. Phase C consisting of $C_{10-40}$ isoalkylamidopropyl ethyldimonium ethosulfate and dipropylene glycol: Phase C is added to the above mixture of Phase A and Phase B until homogeneous composition above is obtained.

Example 31—Hair Cream A

An exemplary styling cream containing a fluorinated compound may include:

| | |
|---|---|
| Water | 93.35% w/w |
| Myristyl Alcohol | 1.00% w/w |
| PEG-8 Stearate | 0.50% w/w |
| Polysorbate 20 | 0.08% w/w |
| Polyacrylate-13 | 1.00% w/w |
| Polyisobutene | 0.50% w/w |
| PPG-2 Myristyl Ether Propionate | 0.50% w/w |
| Phenoxyethanol | 0.50% w/w |
| Caprylyl Glycol | 0.20% w/w |
| Sorbic Acid | 0.05% w/w |
| Fluorinated compound | 2.00% w/w |
| Fragrance | 0.30% w/w |

The fluorinated compound is as described in Example 2 above.

The above composition may be manufactured using the process described below.

Phase A consisting of water: First, a vessel is charged with water. Then, the vessel is heated to 50° C. Phase B consisting of a mixture of myristyl alcohol, PEG-8 stearate, polysorbate 20, polyacrylate-13 and polyisobutene: Phase B ingredients are added to Phase A, allowing myristyl alcohol and PEG-8 stearate to melt before adding polysorbate 20, polyacrylate-13 and polyisobutene. The contents are mixed with high agitation for 30 minutes or until homogeneous. Phase C consisting of PPG-2 myristyl ether propionate is added to the above mixture of Phase A and Phase B and the contents are mixed until homogeneous. The mixture is cooled to 45° C. Then Phase D consisting of phenoxyethanol, caprylyl glycol and sorbic acid is added to the above mixture and the contents are mixed until homogeneous. The mixture is cooled to 30° C. Then Phase E consisting of the fluorinated compound and fragrance is added to the above mixture and the contents are mixed until homogeneous. Then water is added q.s. to the mixture and homogenized to obtain the above composition.

Example 32—Hair Cream B

An exemplary styling cream containing a fluorinated compound may include:

| | |
|---|---|
| Water | 93.05% w/w |
| Cetyl Alcohol | 0.80% w/w |
| Polysorbate 20 | 0.10% w/w |
| Polyacrylate-13 | 1.10% w/w |
| Polyisobutene | 0.60% w/w |
| Octyl Stearate | 1.25% w/w |
| Phenoxyethanol | 0.50% w/w |
| Caprylyl Glycol | 0.20% w/w |
| Sorbic Acid | 0.05% w/w |
| Fluorinated compound | 2.00% w/w |
| Fragrance | 0.35% w/w |

The fluorinated compound is as described in Example 2 above.

The above composition may be manufactured using the process described below.

Phase A consisting of water: First, a vessel is charged with water. Then, the vessel is heated to 60° C. Phase B consisting of a mixture of cetyl alcohol, polysorbate 20, polyacrylate-13 and polyisobutene: Phase B ingredients are added to Phase A, allowing cetyl alcohol to melt before adding polysorbate 20, polyacrylate-13 and polyisobutene. The contents are mixed with high agitation for 30 minutes or until homogeneous. Phase C consisting of octyl stearate is added to the above mixture of Phase A and Phase B until homogeneous. The mixture is cooled to 45° C. Then Phase D consisting of phenoxyethanol, caprylyl glycol and sorbic acid is added to the above mixture and the contents are mixed until homogeneous. The mixture is cooled to 30° C. Then Phase E consisting of the fluorinated compound and fragrance is added to the above mixture and the contents are mixed until homogeneous. Then water is added q.s. to the mixture and homogenized to obtain the above composition.

Example 33—Hair Cream C

An exemplary hair styling control cream containing a fluorinated compound may include:

| | |
|---|---|
| Water | 76.30% w/w |
| VP/VA Copolymer | 6.00% w/w |
| VP/Dimethylaminoethyl methacrylate Copolymer | 10.00% w/w |
| Myristyl Alcohol | 1.00% w/w |
| PEG-8 Stearate | 0.50% w/w |
| Polysorbate 20 | 0.08% w/w |
| Polyacrylate-13 | 1.00% w/w |
| Polyisobutene | 0.50% w/w |
| PPG-2 Myristyl Ether Propionate | 0.50% w/w |
| Phenoxyethanol | 0.50% w/w |
| Caprylyl Glycol | 0.20% w/w |

| | |
|---|---|
| Sorbic Acid | 0.05% w/w |
| Fluorinated compound | 2.00% w/w |
| Glycerin | 1.00% w/w |
| Fragrance | 0.35% w/w |

The fluorinated compound is as described in Example 2 above.

The above composition may be manufactured using the process described below.

Phase A consisting of water, VP/VA copolymer, and VP/dimethylaminoethyl methacrylate copolymer: First, a vessel is charged with water. Then, VP/VA copolymer, and VP/dimethylaminoethyl methacrylate copolymer are added to the vessel. The vessel is then heated to 50° C. Phase B consisting of a mixture of myristyl alcohol, PEG-8 stearate, polysorbate 20, polyacrylate-13 and polyisobutene: Phase B ingredients are added to Phase A, allowing myristyl alcohol and PEG-8 stearate to melt before adding polysorbate 20, polyacrylate-13 and polyisobutene. The contents are mixed with high agitation for 30 minutes or until homogeneous. Phase C consisting of PPG-2 myristyl ether propionate is added to the above mixture of Phase A and Phase B until homogeneous. The mixture is cooled to 45° C. Then Phase D consisting of phenoxyethanol, caprylyl glycol and sorbic acid is added to the above mixture and the contents are mixed until homogeneous. The mixture is cooled to 30° C. Then Phase E consisting of the fluorinated compound, glycerin and fragrance is added to the above mixture and the contents are mixed until homogeneous. Then water is added q.s. to the mixture and homogenized to obtain the above composition. The foregoing has been a description of certain non-limiting preferred embodiments of the invention. Those of ordinary skill in the art will appreciate that various changes and modifications to this description may be made without departing from the spirit or scope of the present invention, as defined in the following claims.

Example 34—Hair Cream D

An exemplary hair styling control cream containing a fluorinated compound may include:

| | |
|---|---|
| Water | q.s. |
| VP/VA Copolymer | 0.00-15.00% w/w |
| VP/Dimethylaminoethyl methacrylate Copolymer | 0.00-15.00% w/w |
| Cetyl Alcohol | 1.50-5.00% w/w |
| PEG-8 Stearate | 0.00-3.50% w/w |
| Polysorbate 20 | 0.00-6.00% w/w |
| Polyacrylate-13 | 0.00-4.00% w/w |
| Polyisobutene | 0.00-5.00% w/w |
| Octyl Stearate | 0.00-2.00% w/w |
| PPG-2 Myristyl Ether Propionate | 0.00-10.00% w/w |
| Phenoxyethanol | 0.00-1.00% w/w |
| Caprylyl Glycol | 0.00-0.50% w/w |
| Sorbic Acid | 0.00-0.1% w/w |
| Fluorinated compound | 0.20-10.00% w/w |
| Glycerin | 0.00-10.00% w/w |
| Fragrance | 0.00-4.00% w/w |

The fluorinated compound is as described in Example 2 above

The above composition may be manufactured using the process described below.

Phase A consisting of water, VP/VA copolymer, and VP/dimethylaminoethyl methacrylate copolymer: First, a vessel is charged with water. Then, VP/VA copolymer, and VP/dimethylaminoethyl methacrylate copolymer are added to the vessel. The vessel is then heated to 50° C. Phase B consisting of a mixture of myristyl alcohol, PEG-8 stearate, polysorbate 20, polyacrylate-13 and polyisobutene: Phase B ingredients are added to Phase A, allowing myristyl alcohol and PEG-8 stearate to melt before adding polysorbate 20, polyacrylate-13 and polyisobutene. The contents are mixed with high agitation for 30 minutes or until homogeneous. Phase C consisting of PPG-2 myristyl ether propionate is added to the above mixture of Phase A and Phase B until homogeneous. The mixture is cooled to 45° C. Then Phase D consisting of phenoxyethanol, caprylyl glycol and sorbic acid is added to the above mixture and the contents are mixed until homogeneous. The mixture is cooled to 30° C. Then Phase E consisting of the fluorinated compound, glycerin and fragrance is added to the above mixture and the contents are mixed until homogeneous. Then water is added q.s. to the mixture and homogenized to obtain the above composition. The foregoing has been a description of certain non-limiting preferred embodiments of the invention. Those of ordinary skill in the art will appreciate that various changes and modifications to this description may be made without departing from the spirit or scope of the present invention, as defined in the following claims.

Example 35—Shampoo

Another exemplary formulation of shampoo containing a fluorinated compound may include:

| Ingredients | % w/w |
|---|---|
| Water | 70.00-95.00 |
| Cocamidopropylamine Oxide | 0.00-20.00 |
| Cocamidopropyl Betaine | 0.00-20.00 |
| Sodium Lauroyl Sarcosinate | 0.00-20.00 |
| PG-Hydroxyethyl Cellulose | 0.00-3.00 |
| Cocodimonium Chloride | |
| PEG-150 Pentaerythrityl Tetrastearate | 0.00-2.00 |
| PEG-6 Caprylic/Capric Glycerides | 0.00-3.00 |
| PEG-90M | 0.00-0.40 |
| Polyquaternium-70 | 0.00-4.00 |
| Hydrolyzed Wheat Protein | 0.00-4.00 |
| $C_{10-40}$ Isoalkylamidopropyl ethyldimonium Ethosulfate | 0.00-1.00 |
| Citric Acid | 0.00-1.00 |
| Fragrance | 0.10-1.50 |
| Preservative | 0.00-2.00 |
| Fluorinated compound | 0.10-10.00 |

The fluorinated compound is as described in Example 2 above.

Example 36—Conditioner

Another exemplary formulation of conditioner containing a fluorinated compound may include:

| Ingredients | % w/w |
|---|---|
| Water | 70.00-95.00 |
| Cetearyl Alcohol | 0.00-10.00 |
| Behentrimonium Chloride | 0.00-3.00 |
| Quaternium-87 | 0.00-1.50 |
| Guar Hydroxypropyltrimonium Chloride | 0.00-1.00 |
| Hydrolyzed Wheat Protein | 0.00-4.00 |
| Citric Acid | 0.00-1.00 |
| Preservative | 0.00-2.00 |
| Fragrance | 0.10-1.50 |
| Fluorinated compound | 0.10-10.00 |

The fluorinated compound is as described in Example 2 above.

Comparative Example 1—Moisture Resistance

The humidity resistance of hair swatch treated with a preferred embodiment of the present invention (Hair Spray A) was compared to that of hair swatch treated with a competitor product (Commercial Example A) as well as with untreated hair swatch using the Dynamic Vapor Sorption (DVS) Protocol I, discussed above. The amounts of products applied (scaled based on package instructions) are shown in Table 1. Target amount of product is as follows: 100 mg (Commercial Example A), and 370 mg (Hair Spray A).

TABLE 1

Overview of samples analyzed by DVS. Amounts were scaled down from package instructions.

| Product | Applications | Shampoo | Target Amount (mg) | Application amounts (mg) | | | | |
|---|---|---|---|---|---|---|---|---|
| | | | | 1 | 2 | 3 | 4 | 5 |
| Hair Spray A | 5 | No | 370 | 380 | 380 | 350 | 360 | 380 |
| Hair Spray A | 5 | Yes | 370 | 350 | 370 | 380 | 360 | 360 |
| Commercial Example A | 5 | Yes | 100 | 100 | 120 | 120 | 90 | 90 |
| Hair Spray A | 1 | No | 370 | 370 | | | | |
| Commercial Example A | 1 | No | 100 | 100 | | | | |
| Water | 1 | No | 320 | 320 | | | | |

As discussed under "Moisture Resistance" above, differences in water adsorption/desorption at a particular relative humidity (the "hysteresis") can be used as a measure to evaluate the ability of a hair treatment to resist or control moisture on and in the hair. In FIG. 1, the lower overall hysteresis values for the Hair Spray A treated samples indicate that less water was able to adsorb onto and penetrate into the hair that for the Commercial Example A-treated samples. This is in line with the hypothesis that the invention creates a vapor barrier on the hair fiber. On the other hand, the Commercial Example A-treated samples behave very similarly to the water-treated samples demonstrating poor vapor barrier function. In fact, the 5 treatment Commercial Example A sample with multiple shampoos performed worse than the water treated sample. This is may be a result of the shampooing increasing the hair's porosity and the inability of Commercial Example A treatment to provide an adequate barrier to protect the hair fibers. As seen in FIG. 1, multiple applications of Hair Spray A increased moisture resistance while the silicone-based Commercial Example A did not demonstrate any resistance versus the water-treated sample at 60% and 80% relative humidity.

Comparative Example 2—Weightlessness

The residue and overall weight of preferred embodiments of the present invention were compared to leading, silicone-based commercial products using the Weightless Test I protocol discussed above. The amounts of products used (based on package instructions) are shown in Table 2.

Formulations were incubated in an oven either for 10 minutes (sprays and serum products) or for 30 minutes (cream products) at 55° C., and the mass remaining was determined.

TABLE 2

Products examined and range of amounts used. Amounts used were based on package instructions provided with each product.

| Sample | Package Instructions | Amount used (g) |
|---|---|---|
| Hair Spray A | 15-20 sprays | 1.9-2.5 |
| Hair Spray B | | 2.1-2.2 |
| Hair Cream A | At least a quarter-sized amount | 1.9-2.5 |
| Hair Cream B | | 2.1-3 |
| Hair Cream C | | 2.1-2.7 |
| Commercial Example A | 1-2 pumps | 0.5-1.1 |
| Commercial Example B | Sparingly | 0.3-0.5 |
| Commercial Example H | Small amount | 0.6-0.8 |
| Commercial Example C | 1-2 pumps | 0.3-0.4 |
| Commercial Example D | N/A | 4-4.5 |
| Commercial Example G | Apply evenly | 1.8-3 |
| Commercial Example E | "pea-size" | 1-1.8 |
| Commercial Example F | Pump 1 or 2 times | 3.2-3.8 |

The average mass remaining at the conclusion of the experiment with standard deviation in parentheses (n≥3) is show in Table 3 below.

TABLE 3

Average mass remaining at the conclusion of the experiment with standard deviation shown in parentheses (n ≥ 3).

| | Product | Mean Percent Mass Remaining (standard deviation) |
|---|---|---|
| Sprays after 10 min | Hair Spray A | 13% (6) |
| | Hair Spray B | 17% (3) |
| | Commercial Example B | 72% (19) |
| | Commercial Example A | 59% (12) |
| | Commercial Example H | 72% (38) |
| | Commercial Example C | 57% (13) |
| | Commercial Example D | 55% (7) |
| Creams after 30 min | Hair Cream A | 10% (3) |
| | Pure Treatment | 9% (5) |
| | Commercial Example G | 30% (11) |
| | Commercial Example E | 45% (13) |
| Control | Control Cream | 30% (6) |
| Creams after 30 min | Commercial Example F | 51% (6) |

From the experimental results, it is clear that formulations of the present invention, on average, leave at least 25% less residue by weigh compared to silicone-based products.

Comparative Example 3—Dirt Resistance

The ability of the preferred embodiments of the present invention to resist accumulation of particulates on hair was examined and compared to leading commercial silicone-based anti-frizz products using the Starch Test I and Starch Test II protocols discussed above. The amounts of products used (based on package instructions) are shown in Table 4.

TABLE 4

Amounts of products applied and weights of simulated dirt-treated tresses after shaking (n ≥3).

| Sample | Amount applied to hair (g) | Percent Change in Mass (standard deviation) |
|---|---|---|
| Hair Spray A | 0.36 | 2.8 (1.4) |
| Hair Cream A | 0.29 | 1.4 (0.6) |
| Pure Treatment | 0.23 | 4.5 (1.2) |
| Control Cream | 0.23 | 4.0 (1.1) |
| Commercial Example A | 0.11 | 19.2 (2.7) |
| Commercial Example B | 0.12 | 24.7 (2.2) |
| Water | 0.36 | 5.4 (2.7) |

Figure 3:
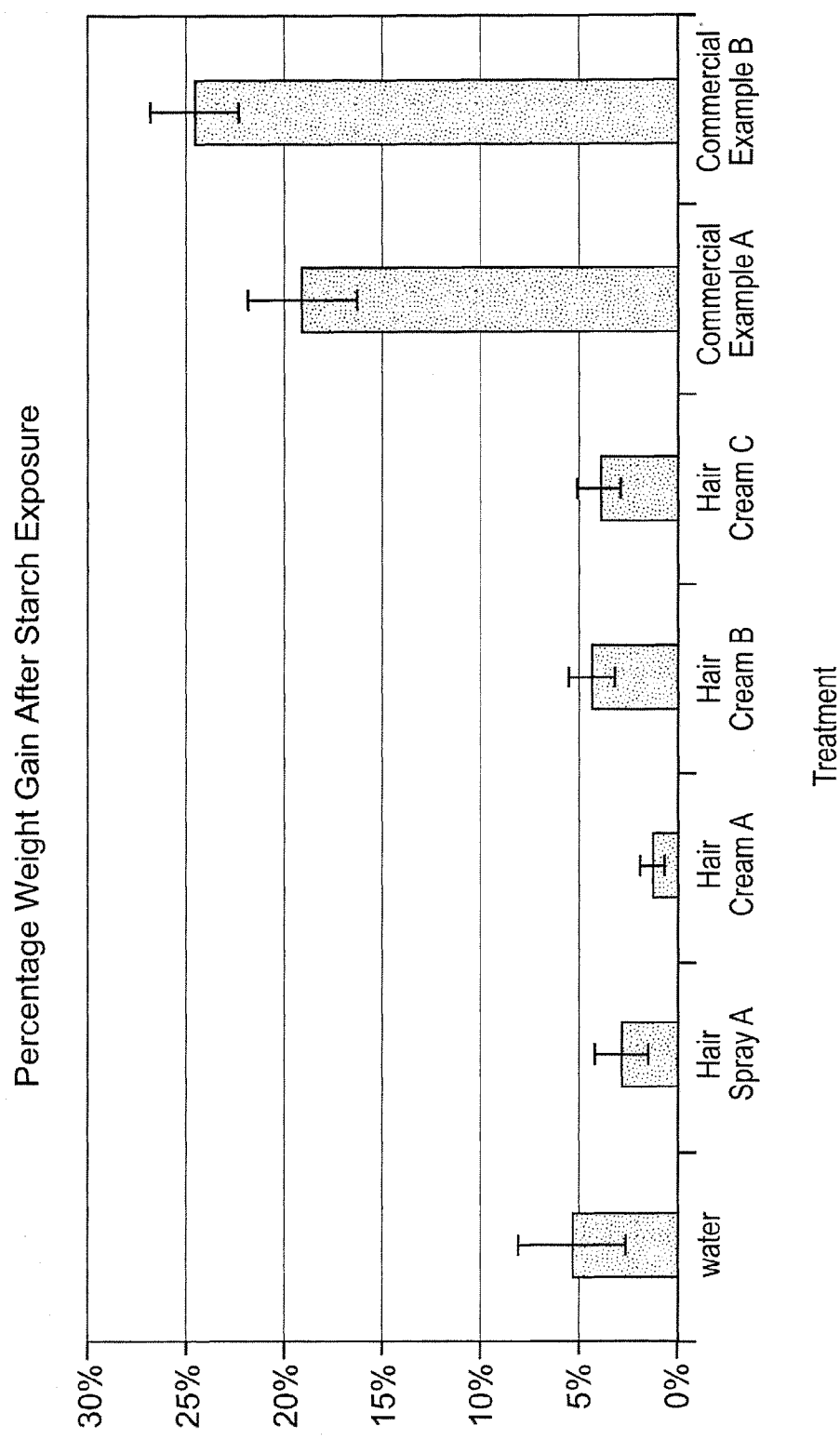
FIG. 3 shows the percent weight gain of hair tresses tested according to Starch Test I (n=3), with embodiments according to the invention and competitor products.

From the experimental results presented in FIG. 3, it is clear that the formulations of the present invention, on average, resist 100% more particulate representative silicone-containing products and 30% more than water alone.

The foregoing has been a description of certain non-limiting preferred embodiments of the invention. Those of ordinary skill in the art will appreciate that various changes and modifications to this description may be made without departing from the spirit or scope of the present invention, as defined in the following claims.

What is claimed is:

1. A method of treating scalp hair comprising the step of: applying to said hair a non-toxic composition comprising a fluorinated, non-polymeric compound with a cosmetically acceptable excipient, wherein the compound is according to one of the formulae:

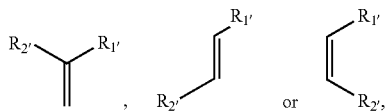

wherein $R_{1'}$ is —$CO_2R_{B'}$; and wherein $R_{B'}$ is

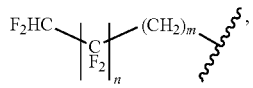

wherein n is an integer between 0 and 20, inclusive; and m is an even or odd integer between 1 and 6, inclusive; and $R_{2'}$ is selected from the group consisting of hydrogen; halogen; substituted or unsubstituted cyclic $C_3$-$C_{20}$ aliphatic; substituted or unsubstituted, branched or unbranched acyclic $C_1$-$C_{20}$ aliphatic; substituted or unsubstituted cyclic $C_3$-$C_{20}$ heteroaliphatic; substituted or unsubstituted, branched or unbranched acyclic $C_1$-$C_{20}$ heteroaliphatic; substituted or unsubstituted, branched or unbranched $C_1$-$C_{20}$ acyl; substituted or unsubstituted $C_6$-$C_{14}$ aryl; substituted or unsubstituted heteroaryl; —$OR_{A'}$; —$C(O)R_{A'}$; —$CO_2R_{A'}$; —$C(O)N(R_{A'})_2$; —$SR_{A'}$; —$SOR_{A'}$; —$SO_2R_{A'}$; —$NR_{A'}$; —$N(R_{A'})_2$; —$NHC(O)R_{A'}$; and —$C(R_{A'})_3$;

wherein heteroaryl is selected from the group consisting of pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, and isoquinolinyl, and wherein each occurrence of $R_{A'}$ is independently selected from a group consisting of hydrogen, substituted or unsubstituted cyclic $C_3$-$C_{20}$ aliphatic; substituted or unsubstituted, branched or unbranched acyclic $C_1$-$C_{20}$ aliphatic; substituted or unsubstituted cyclic $C_3$-$C_{20}$ heteroaliphatic; substituted or unsubstituted, branched or unbranched acyclic $C_1$-$C_{20}$ heteroaliphatic; substituted or unsubstituted, branched or unbranched $C_1$-$C_{20}$ acyl; substituted or unsubstituted $C_6$-$C_{14}$ aryl; substituted or unsubstituted heteroaryl; alkoxy; aryloxy; alkylthio; arylthio; amino; alkylamino; dialkylamino; heteroaryloxy; and heteroarylthio, wherein heteroaryl is as defined above;

provided that the non-toxic composition and method do not employ a free radical initiator, a polymerization initiator or a polymerization catalyst.

2. The method according to claim 1, wherein the compound is selected from the group consisting of 1H,1H,11H-eicosafluoroundecyl acrylate; 1H,1H,11H-eicosafluoroundecyl methacrylate; 2,2,3,3,4,4,5,5-octafluoropentyl methacrylate; 2,2,3,3,4,4,5,5-octafluoropentyl acrylate; 1H,1H,7H-dodecafluoroheptyl acrylate; and 1H,1H,7H-dodecafluoroheptyl methacrylate.

3. The method according to claim 1, wherein the compound is:

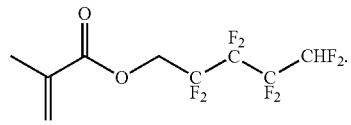

4. The method according to claim 1, wherein said method does not employ a step consisting of rinsing said hair after applying said composition.

5. The method according to claim 1, wherein the method does not further employ a step of (i) applying a composition containing more than about 0.1% weight/weight of a uv-activated free radical initiator that is activated under ambient light, or (ii) applying a composition containing more than about 0.01% weight/weight of a free radical initiator selected from the group consisting of a heat-activated initiator that is activated at or above ambient temperature and an initiator that is active at ambient temperature.

6. A non-toxic hair care composition comprising a fluorinated, non-polymeric compound and a cosmetically acceptable excipient, wherein the compound is according to one of the formulae:

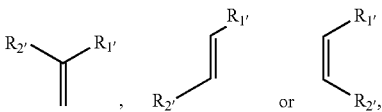

wherein $R_{1'}$ is —$CO_2R_{B'}$; and wherein $R_{B'}$ is

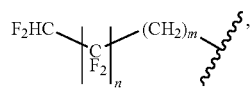

wherein n is an integer between 0 and 20, inclusive; and m is an even or odd integer between 1 and 6, inclusive; and $R_{2'}$ is selected from the group consisting of hydrogen; halogen; substituted or unsubstituted cyclic $C_3$-$C_{20}$ aliphatic; substituted or unsubstituted, branched or unbranched acyclic $C_1$-$C_{20}$ aliphatic; substituted or unsubstituted cyclic $C_3$-$C_{20}$ heteroaliphatic; substituted or unsubstituted, branched or unbranched acyclic $C_1$-$C_{20}$ heteroaliphatic; substituted or unsubstituted, branched or unbranched $C_1$-$C_{20}$ acyl; substituted or unsubstituted $C_6$-$C_{14}$ aryl; substituted or unsubstituted heteroaryl; —$OR_{A'}$; —$C(O)R_{A'}$; —$CO_2R_{A'}$; —$C(O)N(R_{A'})_2$; —$SR_{A'}$; —$SOR_{A'}$; —$SO_2R_{A'}$; —$NR_{A'}$; —$N(R_{A'})_2$; —$NHC(O)R_{A'}$; and —$C(R_{A'})_3$;

wherein heteroaryl is selected from the group consisting of pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, and isoquinolinyl, and wherein each occurrence of $R_{A'}$ is independently selected from a group consisting of hydrogen, substituted or unsubstituted cyclic $C_3$-$C_{20}$ aliphatic; substituted or unsubstituted, branched or unbranched acyclic $C_1$-$C_{20}$ aliphatic; substituted or unsubstituted cyclic $C_3$-$C_{20}$ heteroaliphatic; substituted or unsubstituted, branched or unbranched acyclic $C_1$-$C_{20}$ heteroaliphatic; substituted or unsubstituted, branched or unbranched $C_1$-$C_{20}$ acyl; substituted or unsubstituted $C_6$-$C_{14}$ aryl; substituted or unsubstituted heteroaryl; alkoxy; aryloxy; alkylthio; arylthio; amino; alkylamino; dialkylamino; heteroaryloxy; and heteroarylthio, wherein heteroaryl is as defined above;

provided that the non-toxic hair care composition does not contain a free radical initiator, a polymerization initiator or a polymerization catalyst.

7. The non-toxic hair care composition according to claim 6, wherein the cosmetically acceptable excipient comprises a rheology modifier and a non-ionic emulsifier, wherein the rheology modifier is selected from the group consisting of gyceryl polyacrylate, sodium polyacrylate, carbomer, acrylates copolymer, acrylic acid/vp crosspolymer, and xanthan gum; and the non-ionic emulsifier is selected from the group consisting of Laureth-23, Ocyldodeceth-20, Oleth-10, Peg-40 Hydrogenated Castor Oil, Polaxomer 127, Polysorbate 20, and Ceteareth-20.

8. The non-toxic hair care composition according to claim 6, wherein the compound is selected from the group consisting of 1H,1H,11H-eicosafluoroundecyl acrylate; 1H,1H,11H-eicosafluoroundecyl methacrylate; 2,2,3,3,4,4,5,5-octafluoropentyl methacrylate; 2,2,3,3,4,4,5,5-octafluoropentyl acrylate; 1H,1H,7H-dodecafluoroheptyl acrylate; and 1H,1H,7H-dodecafluoroheptyl methacrylate.

9. The non-toxic hair care composition according to claim 6, wherein the compound is:

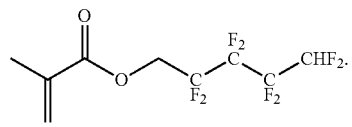 [SMILES: C=C(C)C(=O)OCC(F)(F)C(F)(F)C(F)(F)C(F)F]

10. The method according to claim 1, wherein hair treated with the composition resists moisture penetration, characterized by at least 4 percent decreased moisture flux as measured according to DVS Protocol I.

11. The method according to claim 1, wherein hair treated with the composition resists dirt, characterized by no more than 15 percent weight gain when subjected to Starch Test I.

12. The method according to claim 1, wherein the composition has at least 50% weight loss when subjected to Weightless Test I.

13. The method according to claim 1, wherein said composition is an aerosol spray, a hair spray, non-aerosol spray, pumpable hair spray, serum, wax, emulsion, suspension, lotion, mousse, solution, gel, pomade, cream, conditioner, or shampoo.

14. A method of treating scalp hair comprising the step of applying to said hair a non-toxic composition comprising a fluorinated, non-polymeric compound and a cosmetically acceptable excipient, wherein the compound is selected from the group consisting of:

2,2,3,3,4,4,5,5-octafluoro-1,6-hexyl dimethacrylate;
2,2,3,3,4,4,5,5-octafluoro-1,6-hexyl diacrylate;
2,2,3,3,4,4-hexafluoro-1,5-pentyl diacrylate; and
2,2,3,3,4,4-hexafluoro-1,5-pentyl dimethacrylate;
provided that the composition and method do not employ a free radical initiator, a polymerization initiator or a polymerization catalyst.

15. The non-toxic hair care composition according to claim 6, wherein the composition is an aerosol spray, a hair spray, non-aerosol spray, pumpable hair spray, serum, wax, emulsion, suspension, lotion, mousse, solution, gel, pomade, cream, conditioner, or shampoo.

16. A non-toxic hair care composition comprising a fluorinated, non-polymeric compound and a cosmetically acceptable excipient, wherein the compound is selected from the group consisting of:

2,2,3,3,4,4,5,5-octafluoro-1,6-hexyl dimethacrylate;
2,2,3,3,4,4,5,5-octafluoro-1,6-hexyl diacrylate;
2,2,3,3,4,4-hexafluoro-1,5-pentyl diacrylate; and
2,2,3,3,4,4-hexafluoro-1,5-pentyl dimethacrylate;
provided that the composition does not contain a free radical initiator, a polymerization initiator or a polymerization catalyst.

17. The method according to claim 1, wherein hair treated with the composition has at least 4% decreased moisture flux as measured according to DVS Protocol I and no more than 15% weight gain when subjected to Starch Test I.

18. The method according to claim 1, wherein hair treated with the composition has at least 4% decreased moisture flux as measured according to DVS Protocol I and no more than 15% weight gain when subjected to Starch Test I and the composition has at least 50% weight loss when subjected to Weightless Test I.

19. The non-toxic hair care composition according to claim 6, wherein the cosmetically acceptable excipient is selected from the group consisting of alcohol, PEG-40 Hydrogenated Castor Oil, Fragrance, VP/Vinyl Caprolactam/DMAPA Acrylates Copolymer, PVP/VA, Cetrimonium chloride, PPG-2 Myristyl Ether Propionate, Glycereth-7, Polysorbate 80, Isohexadecane, Acrylamide/Sodium Acryloyldimethyltaurate Copolymer, Phenoxyethanol, Methylparaben, Propylparaben, Polysorbate 20, Polyacrylate-13, Polyisobutene, Ethylhexyl Stearate, Caprylyl Glycol, Sorbic acid, Cetyl alcohol, Cetearyl alcohol, Glyceryl Stearate, Ceteareth-20, Stearyl alcohol, Laureth-23, Laureth-4, Behenyl alcohol, Ceteth-10, PEG-40 Stearate, Hydroxypropyltrimonium Hydrolyzed Corn Starch, PPG-3 Benzyl Ether Myristate, Carbomer, Triethanolamine, Behentrimonium Chloride, PPG-2 Myristyl Propionate, VP/Acrylates/Lauryl Methacrylate Copolymer, Polyquaternium-28, Sodium Polyactylate, Preservative, PEG-4M, Steareth-21, Steareth-20, C10-40 Isoalkylamidopropyl Ethyldimonium Ethosulfate, Cosmetic Fluid CF-76 Cosmetic fluid CF-61, Oleic acid, Sorbitan Oleate, Glyceryl Polyacrylate, Glycerin, Phenoxyethanol, Methylisothiazolinone, Paraffin blend, Acrylic Acid/VP Crosspolymer, Aminomethyl Propanol, SiClone SR-5, Myristyl alcohol, VP/Dimethylaminoethyl Methacrylate Copolymer, PEG-100 Stearate, PEG-40 Stearate, Polyacrylate-13, Acrylamide/Sodium Acryloyldimethyltaurate Copolymer, Isohexadecane, Polyisobutene, Linoleum Acid, Oleth-20, Oleth-2, PEG-8 Beeswax, Capric/Caprylic Triglyceride, Polyquaternium-46, PVP, Cocamidopropylbetaine, Lauramide Oxide, Trideceth-12, PEG-8 Stearate, Fatty acid, Hydroxyethylcellulose, Xanthan Gum, PEG-150 Distearate, Sarcosinate Acid, Glyceryl Oleate, PEG-90M, Hydroxypropylcellulose, PEG-24M, Denatured alcohol, $C_{10\text{-}40}$ Isoalkylamidopropyl ethyldimonium Ethosulfate, Dipropylene Glycol, Octyl Stearate, VP/VA Copolymer, Cocamidopropylamine Oxide, Cocamidopropyl Betaine, Sodium Lauroyl Sarcosinate, PG-Hydroxyethyl Cellulose Cocodimonium Chloride, PEG-150 Pentaerythrityl Tetrastearate, PEG-6 Caprylic/Capric Glycerides, Polyquaternium-70, Hydrolyzed Wheat Protein, and Citric acid.

20. The method according to claim 1, wherein n is an integer between 1 and 20, inclusive.

21. The method according to claim 1, wherein n is an integer between 1 and 20, inclusive; and m is 1.

22. The non-toxic hair care composition according to claim 6, wherein n is an integer between 1 and 20, inclusive.

23. The non-toxic hair care composition according to claim 6, wherein n is an integer between 1 and 20, inclusive; and m is 1.

* * * * *